US009235040B2

(12) United States Patent
Kishima

(10) Patent No.: US 9,235,040 B2
(45) Date of Patent: Jan. 12, 2016

(54) BIOLOGICAL SAMPLE IMAGE ACQUIRING APPARATUS, BIOLOGICAL SAMPLE IMAGE ACQUIRING METHOD, AND BIOLOGICAL SAMPLE IMAGE ACQUIRING PROGRAM

(75) Inventor: Koichiro Kishima, Kanagawa (JP)

(73) Assignee: Sony Corporation, Tokyo (JP)

( * ) Notice: Subject to any disclaimer, the term of this patent is extended or adjusted under 35 U.S.C. 154(b) by 454 days.

(21) Appl. No.: 12/797,799

(22) Filed: Jun. 10, 2010

(65) Prior Publication Data

US 2010/0321484 A1    Dec. 23, 2010

(30) Foreign Application Priority Data

Jun. 23, 2009 (JP) ................................ P2009-148758
Oct. 23, 2009 (JP) ................................ P2009-244873
Jan. 27, 2010 (JP) ................................ P2010-015727

(51) Int. Cl.
*H04N 7/18* (2006.01)
*G02B 21/36* (2006.01)
*G01N 21/64* (2006.01)
*G02B 21/26* (2006.01)

(52) U.S. Cl.
CPC .......... *G02B 21/365* (2013.01); *G01N 21/6458* (2013.01); *G02B 21/26* (2013.01)

(58) Field of Classification Search
None
See application file for complete search history.

(56) References Cited

U.S. PATENT DOCUMENTS

| | | | |
|---|---|---|---|
| 5,481,111 A * | 1/1996 | Rosar et al. | 250/311 |
| 6,961,080 B2 * | 11/2005 | Richardson | 348/80 |
| 7,110,105 B2 * | 9/2006 | Yoshida et al. | 356/237.4 |
| 8,184,920 B2 * | 5/2012 | Oshiro et al. | 382/255 |
| 2003/0040031 A1 * | 2/2003 | Kim et al. | 435/29 |
| 2003/0132382 A1 * | 7/2003 | Sogard | 250/311 |
| 2004/0183902 A1 * | 9/2004 | Bishop | 348/139 |
| 2007/0268495 A1 * | 11/2007 | Rinn | 356/500 |
| 2008/0008349 A1 * | 1/2008 | Binnig et al. | 382/100 |
| 2008/0304147 A1 * | 12/2008 | Kawanabe et al. | 359/388 |
| 2009/0231689 A1 | 9/2009 | Pittsyn et al. | |
| 2011/0115897 A1 * | 5/2011 | Najmabadi et al. | 348/79 |
| 2011/0317904 A1 * | 12/2011 | Zhu et al. | 382/133 |
| 2012/0046191 A1 * | 2/2012 | Vu et al. | 506/9 |

FOREIGN PATENT DOCUMENTS

| | | |
|---|---|---|
| JP | 05-313068 | 11/1993 |
| JP | 09-097332 | 4/1997 |
| JP | 2003-222807 | 8/2003 |
| JP | 2004-507743 | 3/2004 |

(Continued)

OTHER PUBLICATIONS

Japanese Patent Office, Office Action issued in connection with Japanese Patent Application No. 2010-015727, dated Nov. 29, 2013. (3 pages).

*Primary Examiner* — Sath V Perungavoor
*Assistant Examiner* — Janese Duley
(74) *Attorney, Agent, or Firm* — K&L Gates LLP

(57) ABSTRACT

A biological sample image acquiring apparatus includes: an objective lens magnifying a region of a biological sample; an imaging device imaging the region magnified by the objective lens; a movement controller moving the focus of the objective lens in the thickness direction of the target region of the biological sample and moving the image of the region, which magnified by the objective lens to be imaged onto an imaging device, in an in-plane direction; and a biological sample image acquiring unit acquiring a biological sample image of the region by exposing the imaging device to light while the movement controller is moving the image of the region.

17 Claims, 24 Drawing Sheets

MOVEMENT OF FOCAL PLANE IN THIRD EMBODIMENT

(56) References Cited

FOREIGN PATENT DOCUMENTS

| JP | 2004-151263 | 5/2004 |
| JP | 2007-525689 | 9/2007 |
| JP | 2008-185518 | 8/2008 |
| JP | 2011-017982 | 1/2011 |

* cited by examiner

BIOLOGICAL SAMPLE IMAGE ACQUIRING APPARATUS
ACCORDING TO FIRST TO THIRD EMBODIMENTS

BIOLOGICAL SAMPLE IN THICKNESS DIRECTION

FIG.3 CONFIGURATION OF DATA PROCESSOR

FUNCTIONAL CONFIGURATION OF CPU PERFORMING DATA
ACQUIRING PROCESS IN FIRST TO THIRD EMBODIMENTS

ACQUISITION OF IMAGE OF EACH REGION OF BIOLOGICAL SAMPLE

MOVEMENT OF FOCAL PLANE ONLY IN THICKNESS DIRECTION, FLUORESCENT MARKER IMAGE, AND BRIGHT POINT

MOVEMENT OF FOCAL PLANE, FLUORESCENT MARKER IMAGE,
AND BRIGHT POINT IN FIRST EMBODIMENT

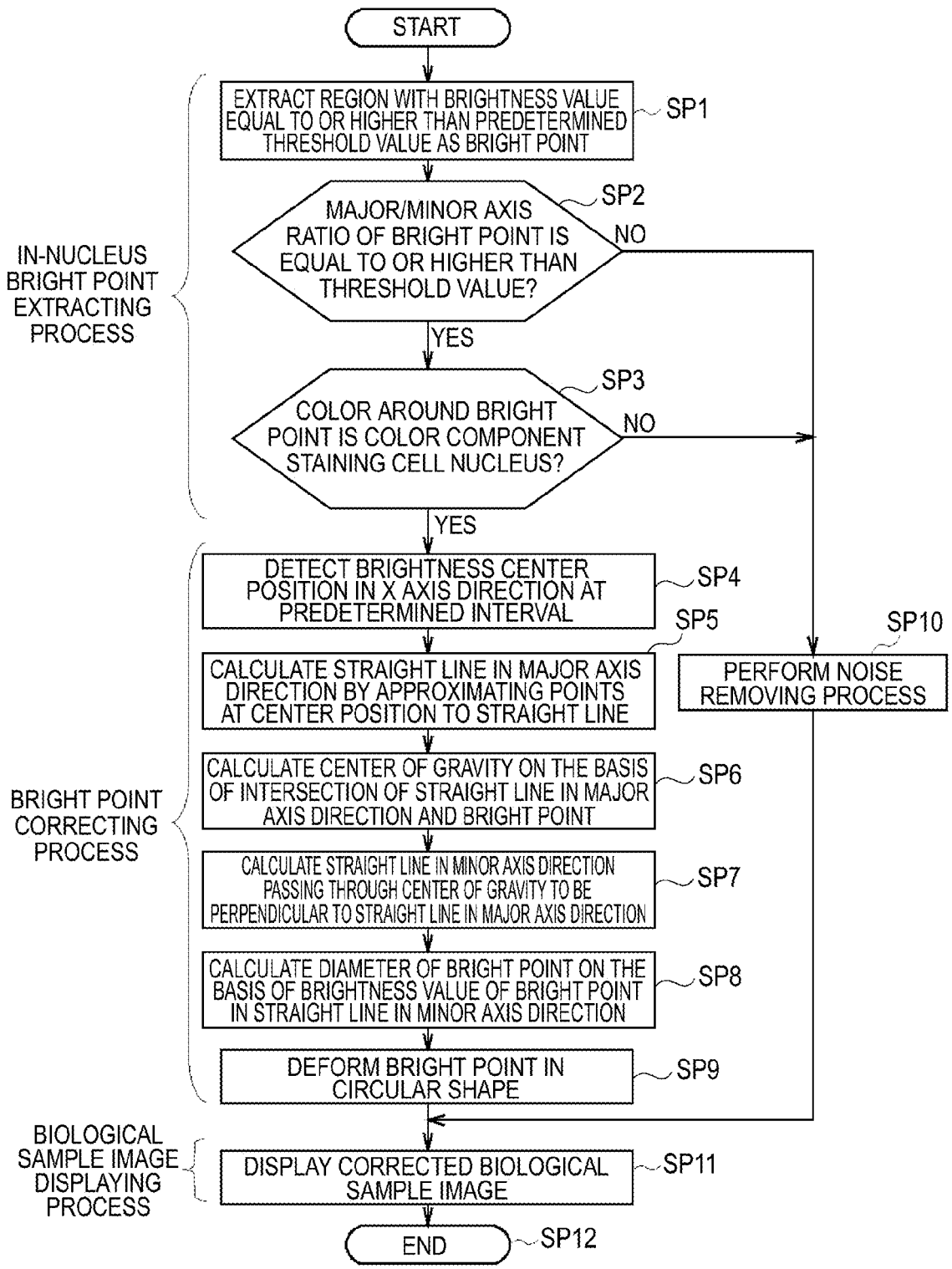

CORRECTION OF BRIGHT POINT

MOVEMENT OF FOCAL PLANE, FLUORESCENT MARKER IMAGE,
AND BRIGHT POINT IN SECOND EMBODIMENT

MOVEMENT OF FOCAL PLANE IN THIRD EMBODIMENT

FLUORESCENT MARKER IMAGE AND BRIGHT POINT IN THIRD EMBODIMENT

RESISTANCE ACQUIRING MODEL

BIOLOGICAL SAMPLE IMAGE ACQUIRING APPARATUS ACCORDING TO FOURTH EMBODIMENT

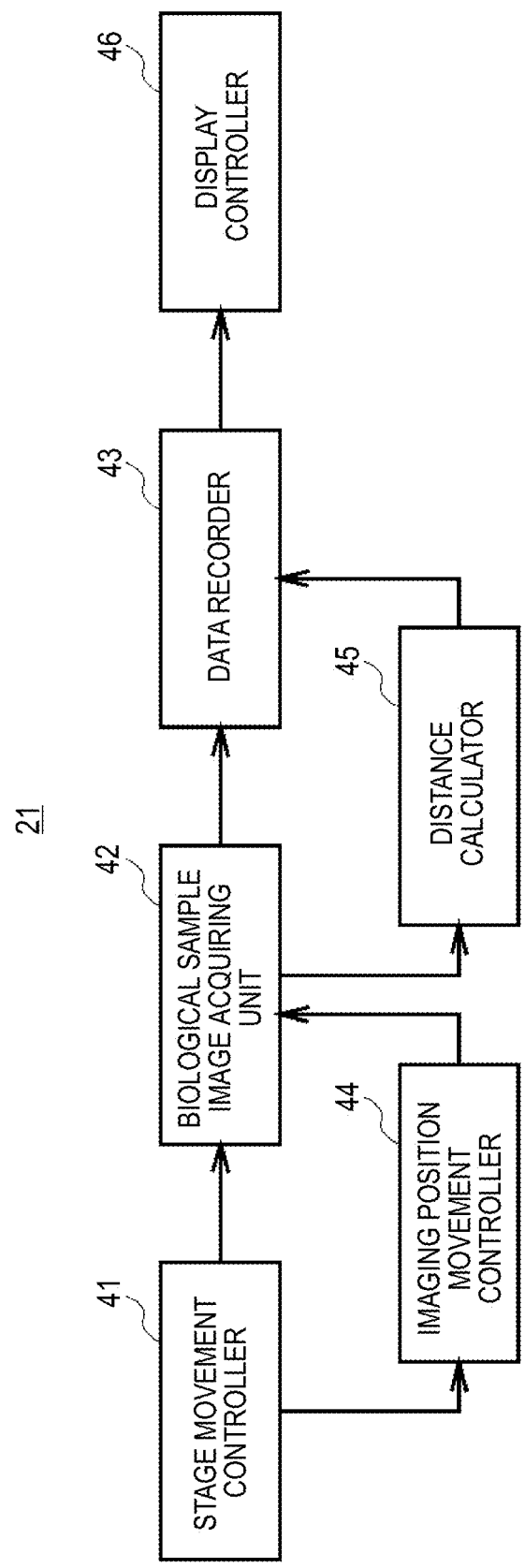

MOVEMENT OF FOCAL PLANE WITH MOVEMENT ONLY IN Z AXIS DIRECTION, BIOLOGICAL SAMPLE IMAGE, AND SHARPENED IMAGE

MOVEMENT OF FOCAL PLANE AND TRANSPARENT PLATE

ELLIPTICAL IMAGE ACQUIRED BY MOVEMENT OF
TRANSPARENT PLATE IN Z AXIS DIRECTION
FIG.18A
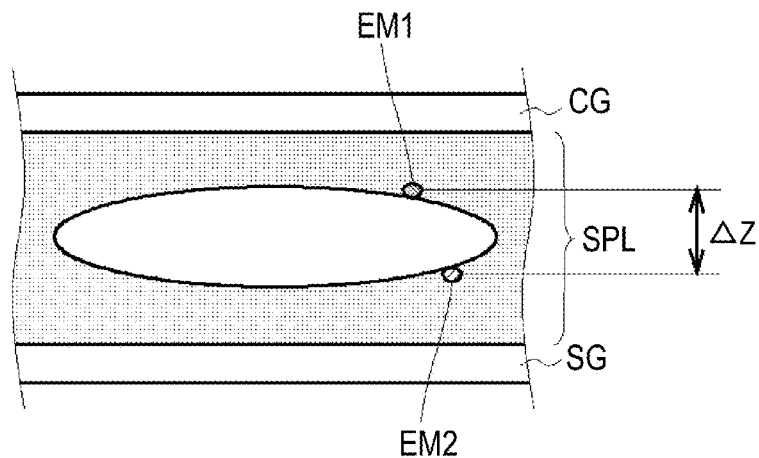
FIG.18B
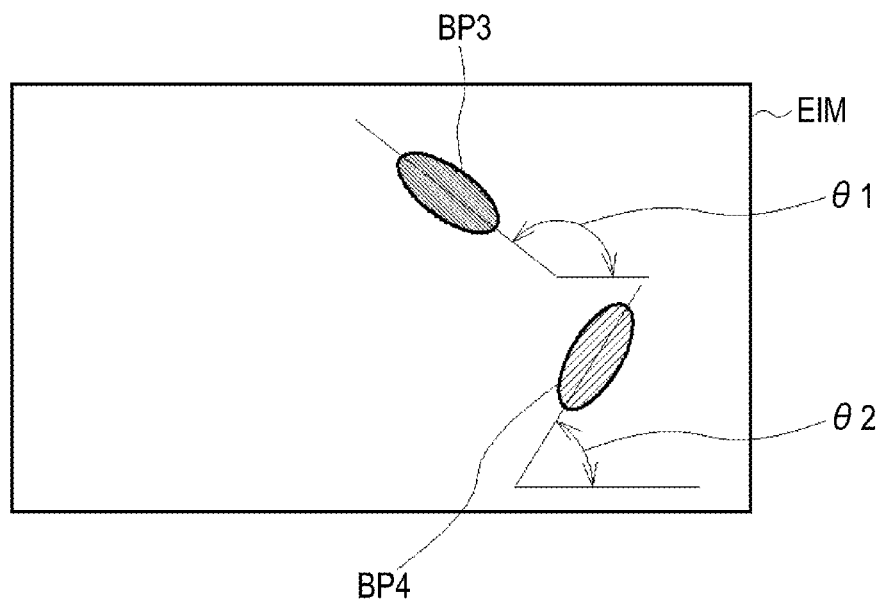
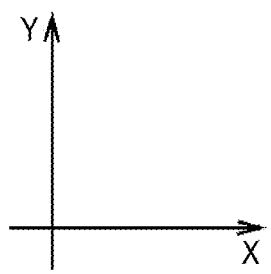

BRIGHT POINTS OF FLUORESCENT MARKERS HAVING DIFFERENT DISTANCE IN Z AXIS DIRECTION

CONFIGURATION OF MICROSCOPE ACCORDING TO ANOTHER EMBODIMENT

FIG.22
CONFIGURATION OF IMAGING POSITION MOVING UNIT IN ANOTHER EMBODIMENT
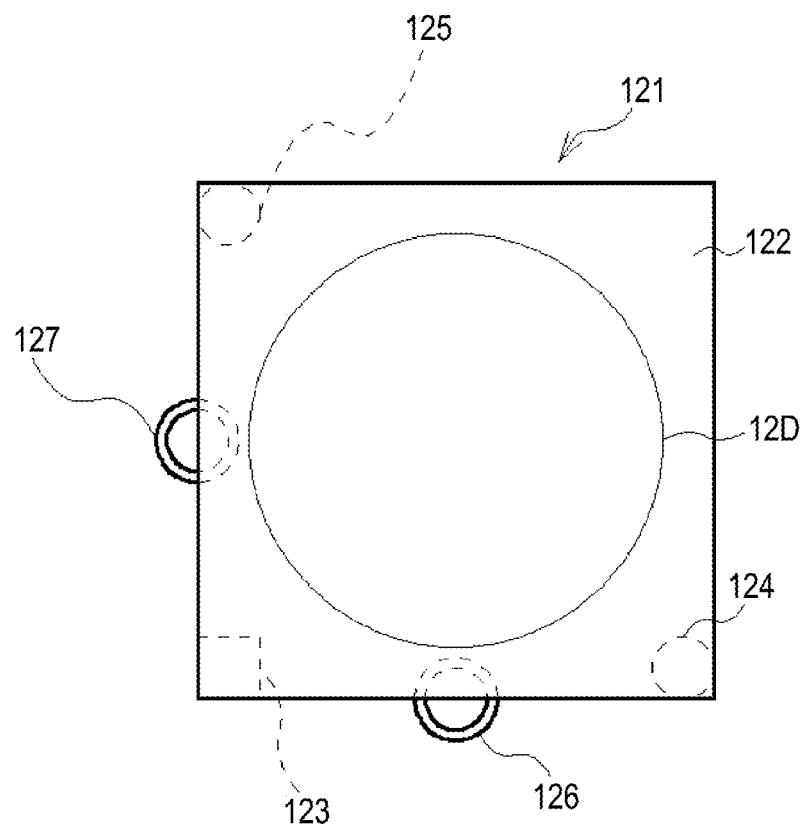
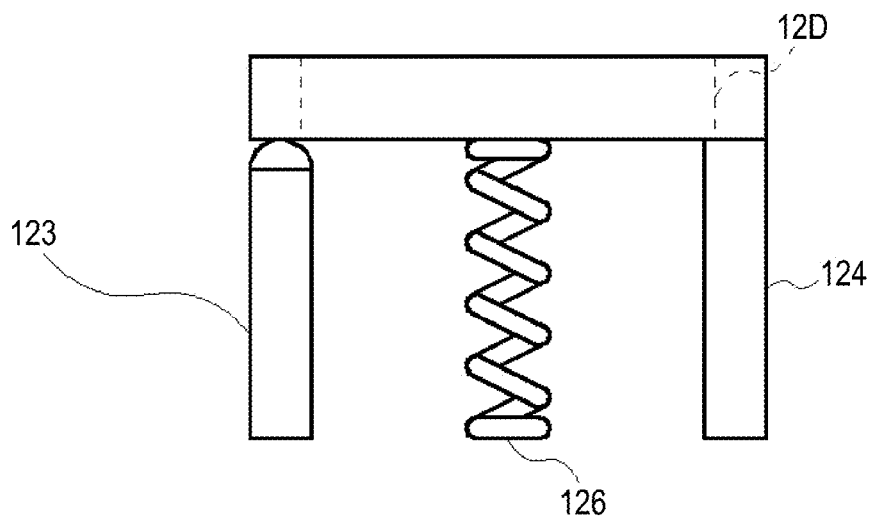

BIOLOGICAL SAMPLE IMAGE IN WHICH FLUORESCENT MARKERS APPEAR AS CIRCULAR IMAGES

TEST SAMPLE

SAMPLE IMAGE

BIOLOGICAL SAMPLE IMAGE WHEN MOVABLE STAGE IS MOVED ONLY IN Z AXIS DIRECTION AND BIOLOGICAL SAMPLE IMAGE WHEN XY PLANE IS CIRCULARLY MOVED WHILE MOVABLE STAGE IS BEING MOVED IN Z AXIS DIRECTION

BIOLOGICAL SAMPLE IMAGE ACQUIRING APPARATUS, BIOLOGICAL SAMPLE IMAGE ACQUIRING METHOD, AND BIOLOGICAL SAMPLE IMAGE ACQUIRING PROGRAM

CROSS REFERENCES TO RELATED APPLICATIONS

The present application claims priority to Japanese Priority Patent Applications JP 2009-148758, JP 2009-244873 and JP 2010-015727 filed in the Japan Patent Office on Jun. 23, 2009, Oct. 23, 2009 and Jan. 27, 2010, respectively, the entire contents of which is hereby incorporated by reference.

BACKGROUND

The present application relates to a biological sample image acquiring apparatus, a biological sample image acquiring method, and a biological sample image program, which can be suitably used in the field of magnification and observation of a biological sample.

A biological sample such as a tissue slice is fixed to a slide glass, is stained as needed, and is then stored. In general, when the storage period is long, the visibility of the biological sample under a microscope is reduced due to deterioration or discoloration of the tissue slice. The biological sample may be diagnosed in establishments other than a hospital in which the biological sample has been prepared. In this case, the biological sample is sent by mail, which takes a predetermined time.

In view of this situation, an apparatus for storing a biological sample as image data was suggested (for example, JP-A-2003-222801).

SUMMARY

In such an apparatus, for example, the number of fluorescent markers existing on a cell nucleus is detected by moving a focus in the thickness direction of a fluorescence-stained biological sample by predetermined intervals and acquiring image data. However, in this method, plural pieces of image data should be stored, thereby increasing the data capacity.

A method of exposing the imaging device to acquire a piece of image data while moving the focus in the thickness direction of the biological sample can be considered. In this method, since a fluorescent marker in the acquired image data is not just in focus but the existence of the fluorescent marker can be checked, it is possible to detect the number of fluorescent markers.

However, in this method, when noise such as signal noise or background noise is generated in the acquired image data, a bright point due to the emission of a fluorescent marker may not be distinguished from a bright point due to the noise, thereby deteriorating the detection precision.

Thus, it is desirable to provide a biological sample image acquiring apparatus, a biological sample image acquiring method, and a biological sample image acquiring program which can improve the detection precision.

According to an embodiment, there is provided a biological sample image acquiring apparatus including: an objective lens magnifying a region of a biological sample; an imaging device imaging the region magnified by the objective lens; a movement controller moving the focus of the objective lens in the thickness direction of the target region of the biological sample and moving the image of the region, which is magnified by the objective lens to be imaged onto an imaging device, in an in-plane direction; and a biological sample image acquiring unit acquiring a biological sample image of the region by exposing the imaging device to light while the movement controller is moving the image of the region.

According to another embodiment, there is provided a biological sample image acquiring method including the steps of: moving the focus of an objective lens in the thickness direction of a target region of a biological sample magnified by the objective lens and moving the image of the region, which is magnified by the objective lens to be imaged onto an imaging device, in an in-plane direction; and acquiring a biological sample image of the region by exposing the imaging device to light during the movement.

According to still another embodiment, there is provided a biological sample image acquiring program causing a computer to perform the steps of: moving the focus of an objective lens in the thickness direction of a target region of a biological sample magnified by the objective lens and moving the image of the region, which is magnified by the objective lens to be imaged onto an imaging device, in an in-plane direction; and acquiring a biological sample image of the region by exposing the imaging device to light during the movement.

Accordingly, since the focus of the objective lens is moved in the thickness direction and the image of the region is moved in the in-plane direction at the time of imaging the region of the biological sample, it is possible to distinguish the biological sample image based on the movement from the noise without being affected by the movement on the basis of the shapes.

According to an embodiment, since the focus of the objective lens is moved in the thickness direction and the image of the region is moved in the in-plane direction at the time of imaging the region of the biological sample, it is possible to distinguish the biological sample image based on the movement from the noise without being affected by the movement on the basis of the shapes. Accordingly, it is possible to provide a biological sample image acquiring apparatus, a biological sample image acquiring method, and a biological sample image acquiring program which can improve the detection precision.

Additional features and advantages are described herein, and will be apparent from the following Detailed Description and the figures.

BRIEF DESCRIPTION OF THE FIGURES

FIG. 8 is a flowchart illustrating a biological sample image correcting and displaying procedure.

FIG. 15 is a diagram schematically illustrating the functional configuration of a CPU performing a data acquiring process according to the fourth embodiment.

FIGS. 18A and 18B are diagrams schematically illustrating an elliptical image acquired due to the movement of the transparent plate in the Z axis direction.

FIG. 22 is a diagram schematically illustrating the configuration of an imaging position moving unit according to another embodiment.

DETAILED DESCRIPTION

The present application is described below in greater detail with reference to the drawings according to an embodiment.

Figure 1:
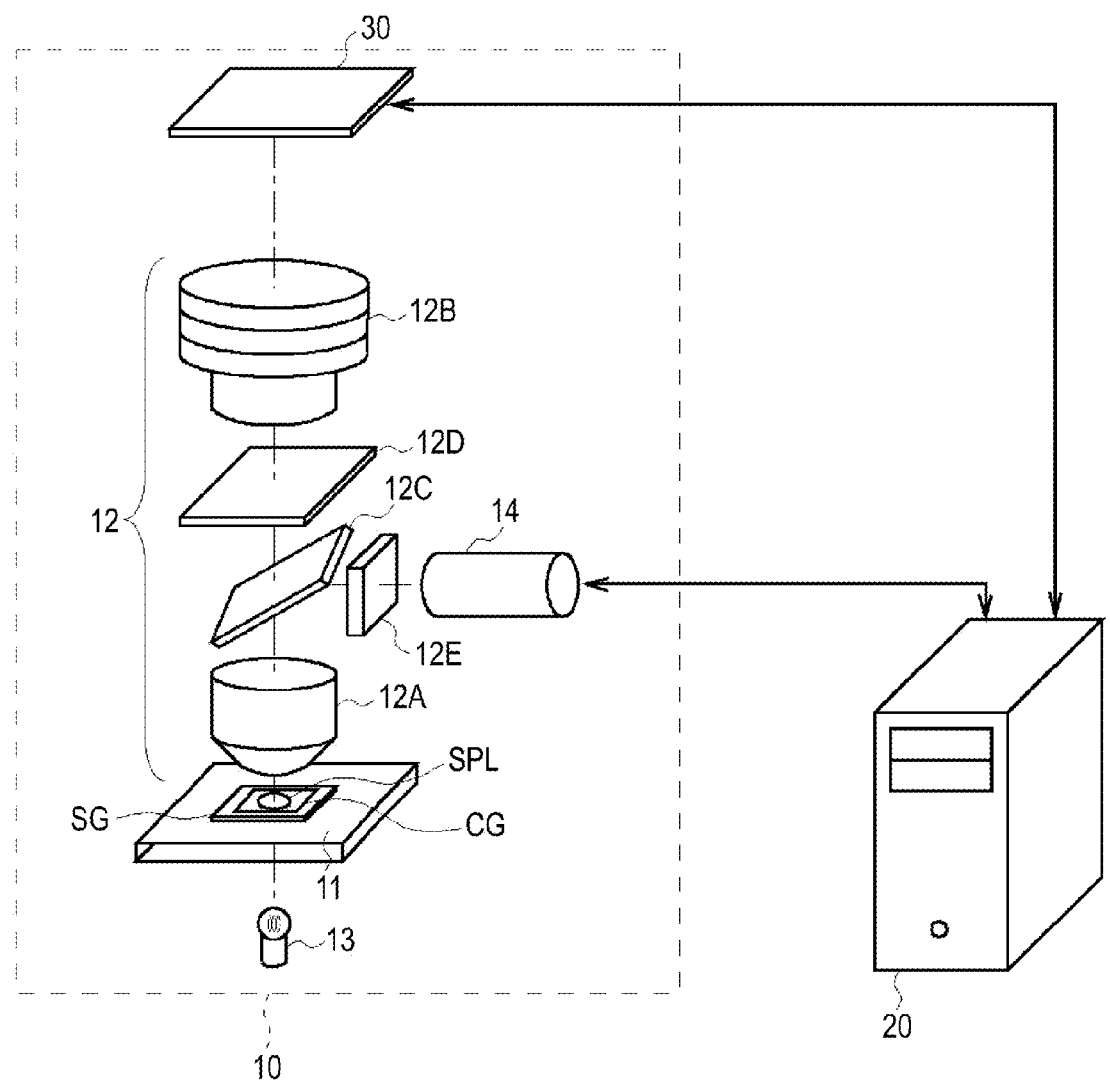
FIG. 1 is a diagram schematically illustrating a biological sample image acquiring apparatus according to first to third embodiments.

1. First Embodiment
2. Second Embodiment
3. Third Embodiment
4. Fourth Embodiment
5. Other embodiments 1. First Embodiment 1-1. Configuration of Biological Sample Image Acquiring Apparatus FIG. 1 shows a biological sample image acquiring apparatus 1 according to an embodiment. The biological sample image acquiring apparatus 1 includes a microscope 10 and a data processor 20.

The microscope 10 includes a stage (hereinafter, also referred to as "movable stage") 11 having a surface on which a biological sample SPL such as a tissue slice or biological polymers of cells or chromosomes is placed and moving in directions (xyz axis directions) parallel or perpendicular to the surface.

Figure 2:
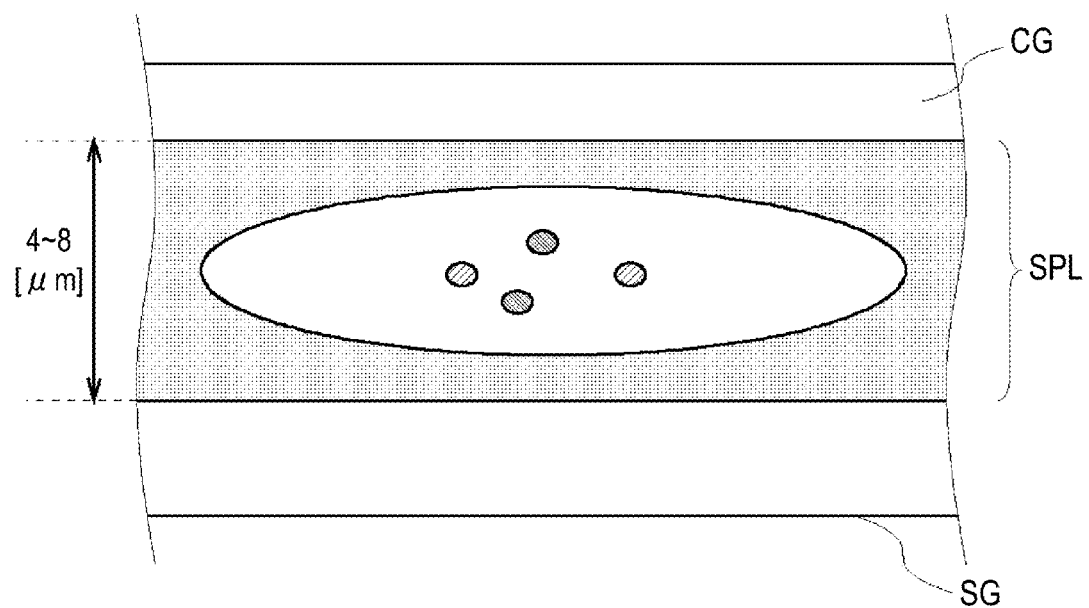
FIG. 2 is a diagram schematically illustrating a biological sample in a thickness direction.

As shown in FIG. 2, the biological sample SPL has a thickness of about 4 to 8 μm in the thickness (depth) direction, is fixed to be interposed between a slide glass SG and a cover glass CG by a predetermined fixing technique, and is stained as needed. Examples of the staining technique include fluorescence staining such as a FISH (Fluorescence In-Situ Hybridization) technique and an enzyme antibody technique, in addition to general staining techniques such as hematoxylin-eosin (HE) staining, Giemsa staining, and Papanicolaou staining.

An optical system 12 is disposed on one side of the movable stage 11 and an illuminating lamp 13 is disposed on the other side of the movable stage 11. The light from the illuminating lamp 13 arrives as illumination light for the biological sample SPL disposed on one side of the movable stage 11 from an opening formed in the movable stage 11.

The microscope 10 magnifies a partial image of the biological sample SPL acquired by the illumination light at a predetermined magnification by the use of an objective lens 12A and an imaging lens 12B of the optical system 12. The microscope 10 focuses the image magnified by the objective lenses 12A and 12B onto an imaging surface of an imaging device 30.

On the other hand, a light source 14 and an excitation filter 12E are disposed at predetermined positions of the microscope 10. In the microscope 10, when light is emitted from the light source 14, exciting light out of the emitted light obtained by causing the excitation filter 12E to transmit only light of an excitation wavelength for fluorescence staining is reflected by a dichroic mirror 12C disposed between the objective lens 12A and the imaging lens 12B and is guided to the objective lens 12A. In the microscope 10, the objective lens 12A concentrates the exciting light on the biological sample SPL placed on the movable stage 11.

When the biological sample SPL fixed to the slide glass SG has been subjected to the fluorescence staining, fluorescent pigments emit light due to the exciting light. Light (hereinafter, referred to as "colored light") acquired by the emission of light passes through the dichroic mirror 12C via the objective lens 12A. The colored light arrives at the imaging lens 12B via an emission filter plate 12D disposed between the dichroic mirror 12C and the imaging lens 12B.

The microscope 10 magnifies an image acquired by the colored light by the use of the objective lens 12A and absorbs light (hereinafter, referred to as "external light") other than the colored light by the use of the emission filter 12D. Then, the microscope 10 magnifies an image acquired by the colored light from which the external light is removed by the use of the imaging lens 12B and forms the magnified image on the imaging surface of the imaging device 30.

On the other hand, the data processor 20 generates an overall image (hereinafter, also referred to as "biological sample image") of the biological sample SPL using the imaging device 30 and stores the biological sample image as a predetermined format of data (hereinafter, also referred to as "sample data").

In this way, the biological sample image acquiring apparatus 1 can store the biological sample SPL placed on the slide glass SG as an image for microscopic testing. Accordingly, the biological sample image acquiring apparatus 1 can store the biological sample SPL for a long time without deteriorating the fixed state or the staining state, compared with the case where the slide glass SG is stored.

1-2. Configuration of Data Processor

Figure 3:
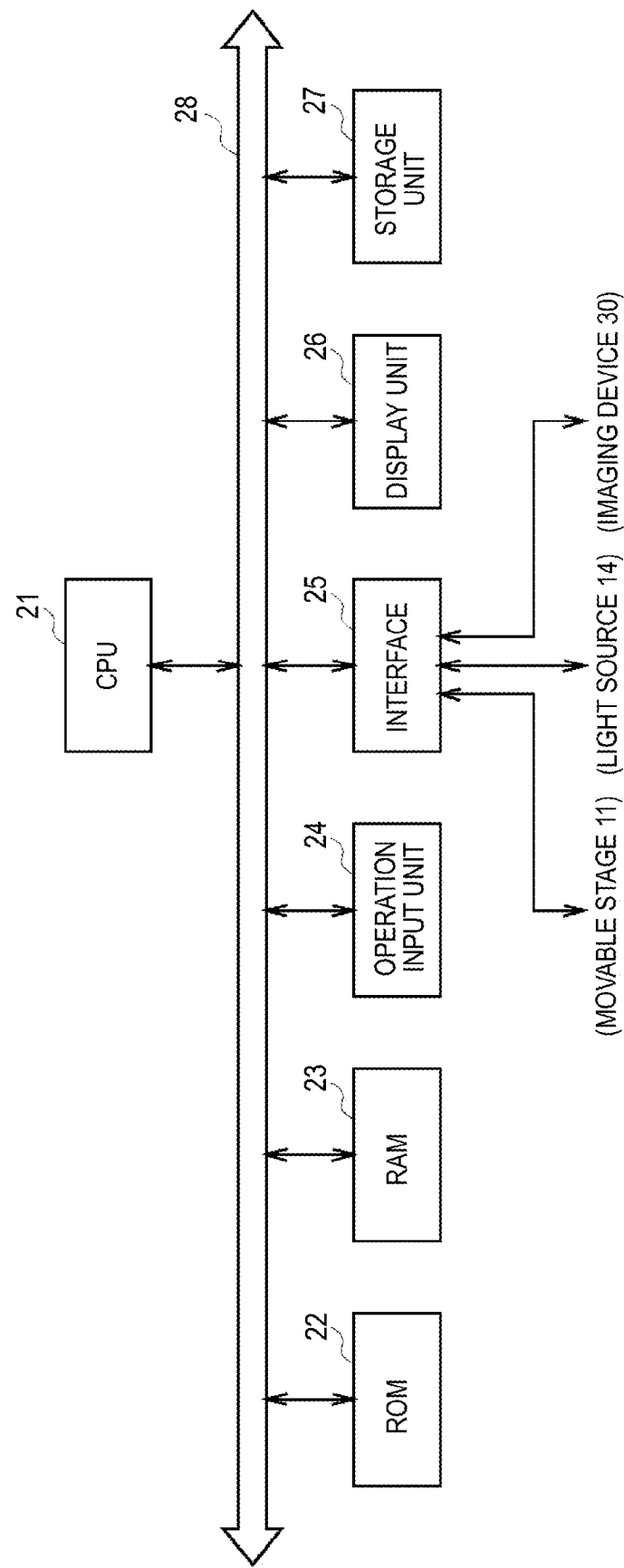
FIG. 3 is a diagram schematically illustrating the configuration of a data processor.

The configuration of the data processor 20 will be described below. As shown in FIG. 3, the data processor 20 is constructed by connecting various hardware elements to a CPU (Central Processing Unit) 21 which performs control.

Specifically, a ROM (Read Only Memory) 22, a RAM (Random Access Memory) 23 serving as a work memory of the CPU 21, an operation input unit 24 for inputting an instruction corresponding to a user's operation, an interface 25, a display unit 26, and a storage unit 27 are connected to the CPU via a bus 28.

Programs for executing various processes are stored in the ROM 22. The movable stage 11, the light source 14, and the imaging device 30 (see FIG. 1) are connected to the interface 25.

A liquid crystal display, an EL (Electro Luminescence) display, or a plasma display is used as the display unit 26. A magnetic disk such as an HD (Hard Disk), a semiconductor memory, or an optical disk is used as the storage unit 27.

The CPU 21 develops a program corresponding to the instruction input from the operation input unit 24 in the RAM 23 out of plural programs stored in the ROM 22 and properly controls the display unit 26 and the storage unit 27 on the basis of the developed program.

The CPU 21 properly controls the movable stage 11, the light source 14, and the imaging device 30 via the interface 25 on the basis of the developed program.

1-3. Data Acquiring Process

Figure 4:
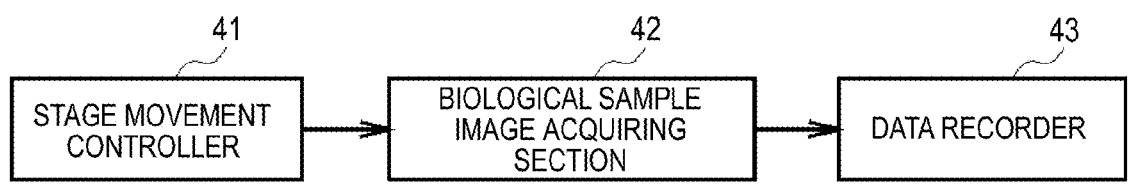
FIG. 4 is a diagram schematically illustrating the functional configuration of a CPU performing a data acquiring process according to the first to third embodiments.

When an instruction to acquire the image of the fluorescence-stained biological sample SPL is received from the operation input unit 24, the CPU 21 serves as a stage movement controller 41, a biological sample acquiring unit 42, and a data recorder 43 on the basis of the program corresponding to the received instruction as shown in FIG. 4.

Figure 5:
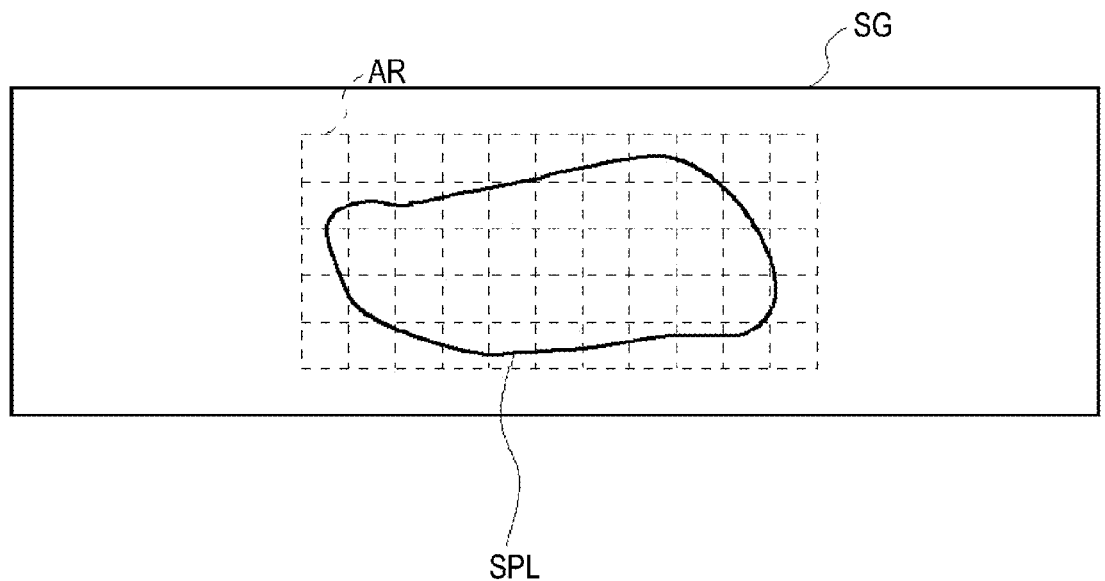
FIG. 5 is a diagram schematically illustrating an example where an image of each region of a biological sample is acquired.

The stage movement controller 41 gradually moves the movable stage 11 so that a target region (hereinafter, also referred to as "sample region") of the biological sample SPL is located in an imaging range AR, and allocates the biological sample SPL to the imaging range AR, for example, as shown in FIG. 5. In FIG. 5, the regions of the biological sample SPL to be allocated to the imaging range AR do not overlap, but some adjacent regions may partially overlap with each other.

The stage movement controller 41 moves the movable stage 11 in the Z axis direction (optical axis direction) and moves the movable stage 11 in the in-plane direction of the XY plane perpendicular to the Z axis direction, whenever the target sample region is moved to the imaging range AR.

Figure 6A:
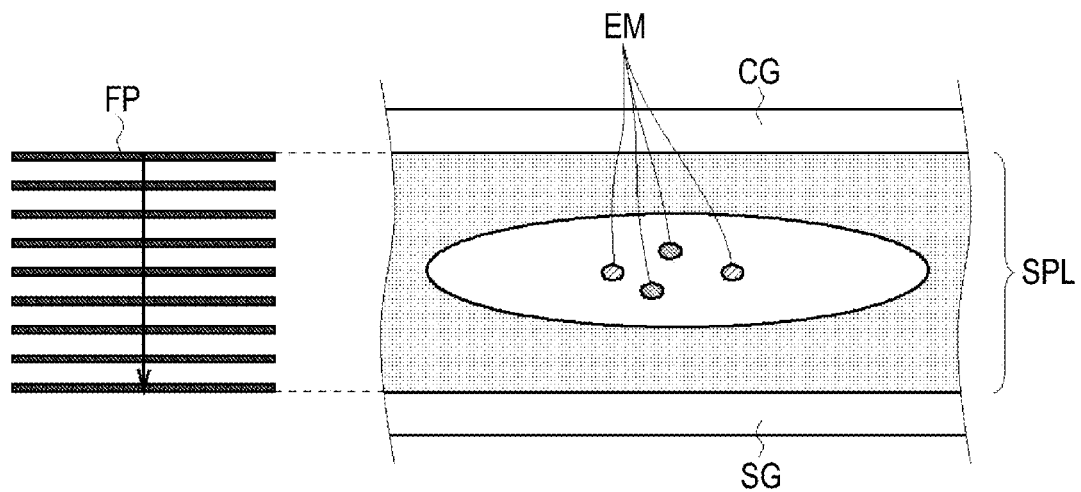
FIGS. 6A, 6B, and 6C are diagrams schematically illustrating movement of a focal plane only in the thickness direction and a fluorescent marker image and a bright point at that time.

In the microscope 10, as shown in FIG. 6A, it is considered that the imaging device 30 is exposed to light to acquire a piece of image data while a focal plane FP of the objective lens 12A is being moved from the cover glass CG to the slide glass SG only in the Z axis direction of the biological sample SPL.

In this method, the objective lens 12A is at first not focused on a fluorescent marker EM coupled to a specific gene, then becomes focused thereon, and then becomes out of focus.

Figure 6B:
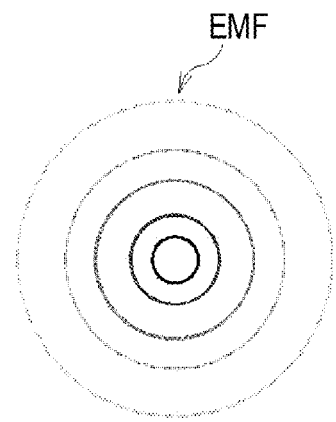

Accordingly, in the imaging device 30, an image EMF (hereinafter, also referred to as "fluorescent marker image") of colored light emitted from the fluorescent marker EM is changed from a blurred large image to a recognizable small image and is then changed to the blurred large state, as shown in FIG. 6B.

Figure 6C:
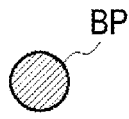

Therefore, in the biological sample image obtained by the imaging, the colored light emitted from the fluorescent marker EM appears as a substantially circular bright point BP, as shown in FIG. 6C.

In the microscope 10, when flickering or noise such as background noise occurs at the time of imaging the biological sample SPL, a bright point based on the noise may appear in the image obtained by imaging the biological sample SPL.

In this method, since the bright point BP based on the fluorescent marker EM is not distinguished from the bright point based on the noise, it is not possible to detect the number of bright points per cell nucleus or the like with high precision.

In the embodiment, the movable stage 11 is moved in the Z axis direction and is also moved in the in-plane direction of the XY plane perpendicular to the Z axis direction.

Specifically, the stage movement controller 41 moves the movable stage 11 in the Z axis direction at a constant speed so as to get close to the objective lens 12A so that the focal plane FP of the objective lens 12A moves from the cover glass CG side of the biological sample SPL to the slide glass SG side. At the same time, the stage movement controller 41 moves the movable stage 11, for example, in the X axis direction which is the in-plane direction of the XY plane at a constant speed.

Figure 7A:
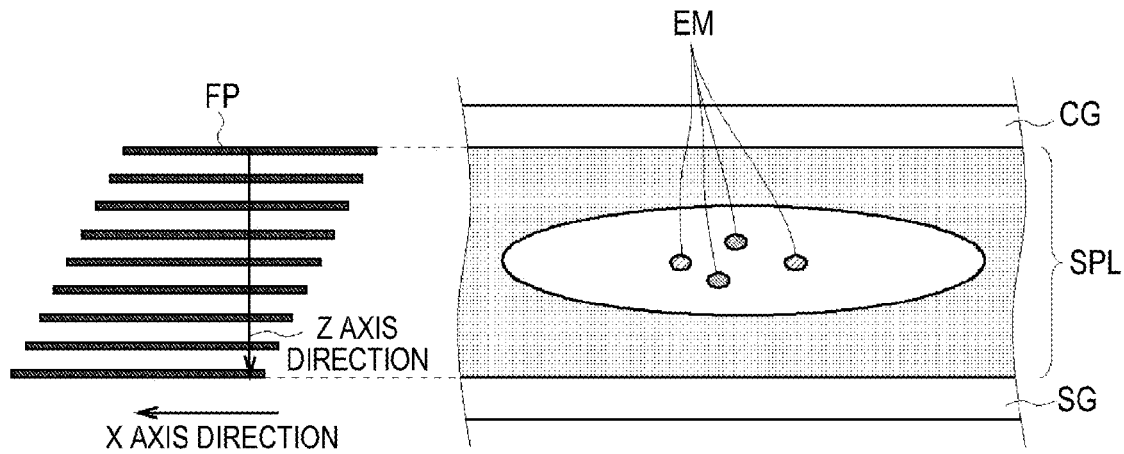
FIGS. 7A, 7B, and 7C are diagrams schematically illustrating movement of a focal plane only in the thickness direction and a fluorescent marker image and a bright point at that time in the first embodiment.

At this time, the focal plane FP of the objective lens 12A is moved in the Z axis direction from the cover glass CG side of the biological sample SPL to the slide glass SG side and is also moved in the X axis direction as the in-plane direction at a constant speed, as shown in FIG. 7A.

The biological sample image acquiring unit 42 exposes the imaging device 30 to light to cause the imaging device 30 to image the target sample region while the movable stage 11 is being moved in the Z axis direction and in the X axis direction, and connects the resultant images of the sample regions to generate a biological sample image.

Figure 7B:
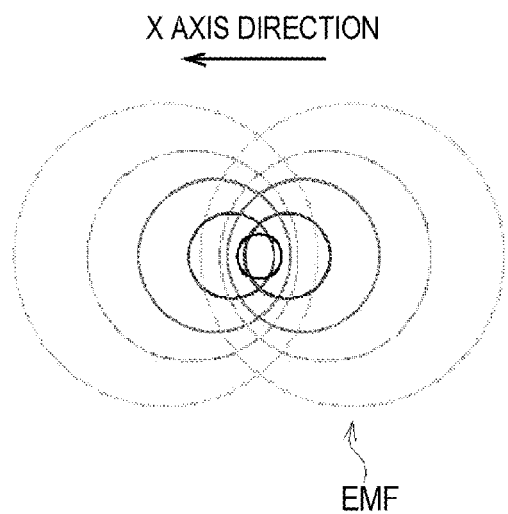
Figure 7C:
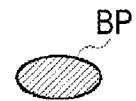

Accordingly, in the imaging device 30, the fluorescent marker is imaged during the movement in the X axis direction while the fluorescent marker image EMF is changed from a blurred large image to a recognizable small image and is then changed to the blurred large image, as shown in FIG. 7B. Accordingly, in the acquired biological sample image, the colored light emitted from the fluorescent marker EM appears as a substantially elliptical bright point BP as shown in FIG. 7C.

Here, it is assumed that the magnification power of the optical system 12 is 20, the pixel pitch of the imaging device 30 is about 6 µm, the diameter of a bright point BP when colored light is imaged in an in-focus state is about 2.1 µm, and the thickness of the biological sample SPL is 8 µm.

The stage movement controller 41 moves the movable stage 11 by 1 µm in the X axis direction while moving the movable stage 11 by 1 µm in the Z axis direction. As a result, the stage movement controller 41 moves the movable stage 11 by 8 μm in the X axis direction while moving the movable stage 11 by 8 μm which is the thickness of the biological sample SPL.

At this time, the colored light emitted from the fluorescent marker EM is imaged as a substantially elliptical bright point BP with a major length of about 10 pixels (60 μm) and a minor length of about 7 pixels (42 μm) onto the imaging device 30. That is, a substantially elliptical bright point BP with a ratio of major and minor lengths (hereinafter, also referred to as "major/minor axis ratio") of about 1.43 is drawn in the biological sample image.

When the biological sample image is generated, the data recorder 43 generates sample data including pixel information representing all of the biological sample image or a part capable of reproducing the biological sample image.

The data recorder 43 adds data representing identification information of the biological sample image to the sample data and records the sample data to which the data is added in the memory unit 27.

The identification information includes information such as the picker name, the picker sex, the picker age, and the picking date of the biological sample SPL. The data recorder 43 provides notification that the identification information should be input at a predetermined time such as a time when a data storing instruction of the biological sample SPL is given or a time when the slide glass SG should be set.

When the identification information is not acquired at the time of generating the sample data, the data recorder 43 gives an alarm about the input of the identification information. That is, the notification or alarm for inputting the identification information is carried out by the use of, for example, a sound or a GUI (Graphical User Interface) picture.

1-4. Biological Sample Image Correcting and Displaying Process

A biological sample image correcting and displaying process of displaying the biological sample image acquired in the data acquiring process on the display unit 26 will be described below. The biological sample image correcting and displaying process will be described with reference to FIG. 8 and FIGS. 9A to 9H.

When an instruction to display a biological sample image is given from the operation input unit 24, the CPU 21 displays the biological sample image on the display unit 26 by performing the biological sample image correcting and displaying process shown in FIG. 8 on the basis of a program corresponding to the instruction.

The biological sample image correcting and displaying process can be divided into an in-nucleus bright point extracting process, a bright point correcting process, and a biological sample image correcting and displaying process.

Specifically, when the flow of processes is started, the CPU 21 performs the in-nucleus bright point extracting process in step SP1, and reads sample data corresponding to a biological sample image to be displayed from the storage unit 27 when the sample data is specified.

The CPU 21 extracts a group of plural pixels having a brightness value equal to or higher than a predetermined threshold value as a bright point BP from the biological sample image based on the read sample data (FIG. 9A), and performs the process of step SP2.

In step SP2, the CPU 21 considers the outline of the extracted bright point BP as an elliptical shape, calculates the major/minor axis ratio of the elliptical shape, and determines whether the major/minor axis ratio is equal to or higher than a predetermined threshold value (for example, 1.3). When the determination result is YES, it means that the bright point BP is based on the colored light emitted from the fluorescent marker EM, and the CPU 21 then performs the process of step SP3.

In step SP3, when a cell nucleus is stained, the CPU 21 detects a color component of peripheral pixels SP of the bright point BP (FIG. 9B) and determines whether the color component is a cell-nucleus staining color component.

When the determination result is YES, it means that the bright point BP is based on the colored light emitted from the fluorescent marker EM existing in a cell nucleus, and the CPU 21 then performs the process of step SP4.

On the other hand, when the determination result in step SP2 is NO, it means that the major-minor axis ratio of the extracted bright point BP is less than the predetermined threshold value. Since the bright point BP is not imaged with the movement of the movable stage 11, the CPU 21 recognizes the bright point as noise and then performs the process of step SP10.

When the determination result in step SP3 is NO, it means that the bright point BP does not exist in the cell nucleus and is light imaged with the movement of the movable stage 11 because of its substantially elliptical shape. For example, the bright point BP is based on the colored light emitted from a remaining fluorescent marker EM. The CPU 21 recognizes the bright point as noise and then performs the process of step SP10.

In this way, the CPU 21 extracts only the bright point BP based on the colored light emitted from the fluorescent marker EM existing in the cell nucleus and recognizes the other bright points BP as noise, by performing the in-nucleus bright point extracting process of steps SP1 to SP3.

Subsequently, by performing the bright point correcting process in step SP4, the CPU 21 detects the brightest pixel in the X axis direction as a center position CP every predetermined interval in the Y axis direction in each bright point BP having a major/minor axis ratio equal to or higher than a threshold value in a cell nucleus (FIG. 9C), and then performs the process of step SP5.

In step SP5, the CPU 21 calculates a straight line SL1 in the major axis direction by approximating the points of the detected center positions CP to a straight line (FIG. 9D), and then performs the process of step SP6.

In step SP6, the CPU 21 calculates the center of the intersections of the outline of the bright point BP and the straight line SL1 in the major axis direction as the center of gravity CT (FIG. 9E), and then performs the process of step SP7.

In step SP7, the CPU 21 calculates a straight line SL2 in the minor axis direction passing through the center of gravity CT so as to be perpendicular to the straight line SL1 in the major axis direction calculated in step SP5 (FIG. 9F), and then performs the process of step SP8.

In step SP8, the CPU 21 calculates the diameter DM of the bright point BP on the basis of the brightness distribution of the bright point BP in the straight line SL2 in the minor axis direction calculated in step SP7 (FIG. 9G), and then performs the process of step SP9.

Figure 9A:
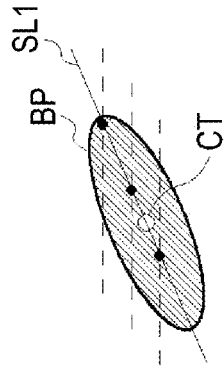
FIGS. 9A to 9H are diagrams schematically illustrating corrections of a bright point.
Figure 9B:
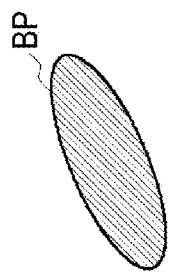
Figure 9C:
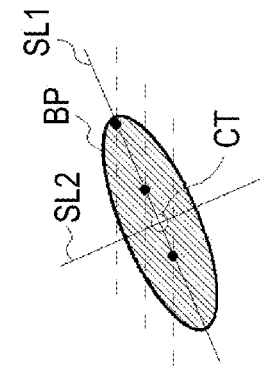
Figure 9D:
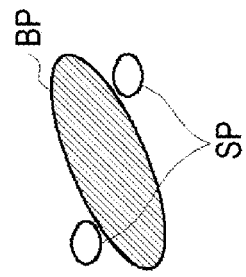
Figure 9E:
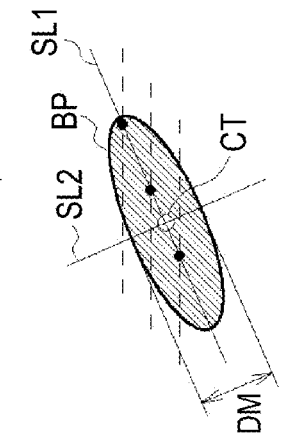
Figure 9F:
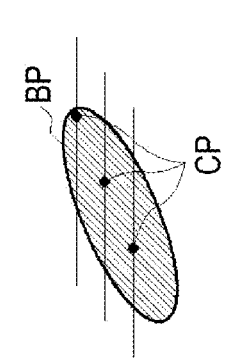
Figure 9G:
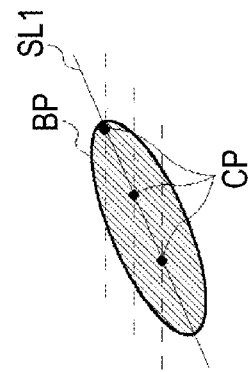
Figure 9H:
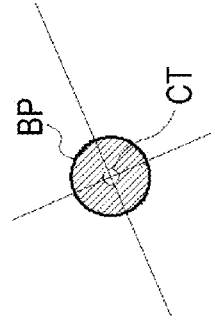

In step SP9, the CPU 21 deforms the bright point BP into a circular shape so as to have the diameter DM and the brightness distribution calculated in step SP8 about the center of gravity CT (FIG. 9H). At this time, the CPU 21 replaces the color of the part excluded from the bright point BP with the background color by deforming the substantially elliptical shape into the circular shape, and then performs the process of step SP11.

On the contrary, when the determination result in step SP2 or SP3 is NO, the CPU 21 performs a noise removing process in step SP10 so as to replace the bright point BP recognized as noise with the background color therearound, and then performs the process of step SP11.

In this way, the CPU 21 performs the bright point correcting process of step SP4 to SP10, deforms the bright point BP in the cell nucleus into the circular shape, and removes the bright point BP recognized as noise, for example, by replacing it with the background color.

In step SP11, the CPU 21 performs the processes of steps SP1 to SP10 on all the bright points BP in the biological sample image, displays the biological sample image on the display unit 26, and then goes to the next step to end the flow of processes. Accordingly, the biological sample image acquiring apparatus 1 can provide only the bright points BP based on the colored light emitted from the fluorescent markers EM coupled to a specific gene.

1-5. Operations and Advantages

In the above-mentioned configuration, the biological sample image acquiring apparatus 1 moves the focal plane FP of the objective lens 12A in the thickness direction of the biological sample SPL and moves it in the in-plane direction, at the time of imaging the biological sample SPL.

The biological sample image acquiring apparatus 1 exposes the imaging device 30 to acquire the biological sample image while moving the focal plane FP in the thickness direction of the biological sample SPL and in the in-plane direction.

Therefore, in the biological sample image acquiring apparatus 1, since the bright point BP based on the fluorescent marker EM wobbles due to the movement and becomes thus elliptical, the bright point BP based on the fluorescent marker EM can be distinguished from the bright point BP based on the noise without being affected by the movement on the basis of the shapes.

Accordingly, the biological sample image acquiring apparatus 1 can remove the bright point based on the noise from the acquired biological sample image, thereby improving the detection precision.

When the cell nucleus is stained, the biological sample image acquiring apparatus 1 can extract the bright point BP based on the fluorescent marker EM existing in the cell nucleus by detecting the color component of the neighboring pixels of the bright point BP based on the fluorescent marker EM and determining whether the detected color component is the cell-nucleus staining color component.

Therefore, the biological sample image acquiring apparatus 1 can extract only the bright points BP based on the fluorescent markers EM existing in a cell nucleus and detect the number of bright points BP existing in the cell nucleus with higher precision, for example.

According to the above-mentioned configuration, the imaging device 30 is exposed to light to acquire the biological sample image while moving the focal plane FP of the objective lens 12A in the thickness direction of the biological sample SPL and moving the relative position between the biological sample SPL and the imaging device 30 in the in-plane direction. Accordingly, since the image based on the movement can be distinguished from the noise, it is possible to improve the detection precision.

2. Second Embodiment

A second embodiment is different from the first embodiment in the movement control of the movable stage 11 in the data acquiring process. They are different from each other regarding some processes regarding the biological sample in the biological sample image correcting and displaying process. The configuration of the biological sample image acquiring apparatus 1 is similar to that of the first embodiment, and thus the description is not repeated.

2-1. Data Acquiring Process

Similarly to the first embodiment, when an instruction to acquire an image of a fluorescence-stained biological sample is received from the operation input unit 24, the CPU 21 serves as the stage movement controller 41, the biological sample acquiring unit 42, and the data recorder 43.

The stage movement controller 41 moves the movable stage 11 in the Z axis direction at a constant speed so as to get close to the objective lens 12A so that the focal plane FP of the objective lens 12A moves from the cover glass CG side of the biological sample SPL to the slide glass SG side. At the same time, the stage movement controller 41 moves the movable stage 11, for example, in the X axis direction which is the in-plane direction of the XY plane while accelerating or decelerating the movable stage at a varying speed.

Figure 10A:
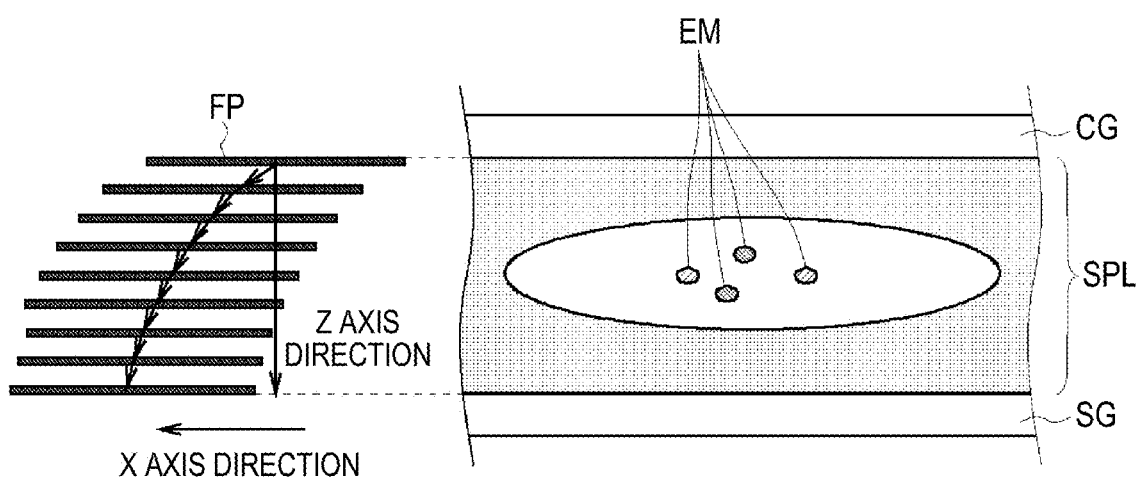
FIGS. 10A, 10B, and 10C are diagrams schematically illustrating movement of a focal plane only in the thickness direction and a fluorescent marker image and a bright point at that time in the second embodiment.

For example, when the movable stage 11 is decelerated in the X axis direction, the focal plane FP of the objective lens 12A is moved from the cover glass CG side of the biological sample SPL to the slide glass SG side in the Z axis direction and is also decelerated in the X axis direction, as shown in FIG. 10A.

The biological sample image acquiring unit 42 exposes the imaging device 30 to light to cause the imaging device 30 to image the sample region while the movable stage 11 is being moved in the Z axis direction and in the X axis direction by the stage movement controller 41, and connects the resultant images of the sample regions to generate a biological sample image.

Figure 10B:
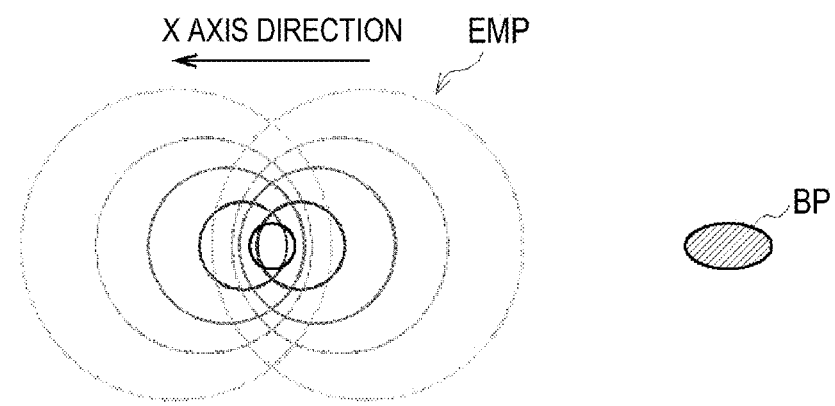

Accordingly, as shown in FIG. 10B, since the fluorescent marker EM close to the cover glass CG is imaged by the imaging device 30 so that the fluorescent marker image EMP is fast moved in the X axis direction, the fluorescent marker appears as a substantially elliptical bright point BP having a long major axis in the biological sample image.

Figure 10C:
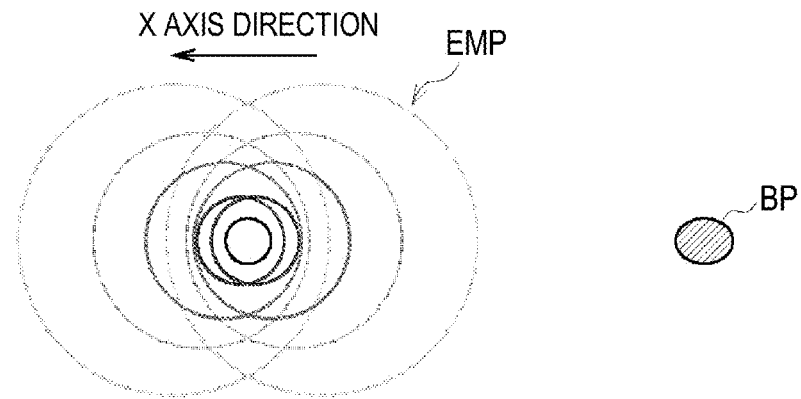

On the contrary, as shown in FIG. 10C, since the fluorescent marker EM close to the slide glass SG is imaged by the imaging device 30 so that the fluorescent marker image EMP is slowly moved in the X axis direction, the fluorescent marker appears as a substantially elliptical bright point BP having a short major axis in the biological sample image.

When the biological sample image is generated, the data recorder 43 generates sample data including pixel information representing all of the biological sample image or a part capable of reproducing the biological sample image.

The data recorder 43 adds data representing identification information of the biological sample image to the sample data and records the sample data to which the data is added in the memory unit 27.

2-2. Biological Sample Image Correcting Displaying Process

The CPU 21 performs the same process as the first embodiment on the basis of the biological sample image correcting and displaying process (FIG. 8), but calculates the position in the thickness direction of a bright point BP of which the major/minor axis ratio is equal to or greater than a threshold value, for example, between the in-nucleus bright point extracting process and the bright point correcting process.

Specifically, the CPU 21 calculates the position in the Z axis direction from a predetermined reference position on the basis of the major/minor axis ratio of the bright point BP extracted in the in-nucleus bright point extracting process and the moving speed in the X direction of the movable stage 11 moved by the stage movement controller 41. In calculating the position in the Z axis direction, for example, a table in which the major/minor axis ratios of the bright points BP are correlated with the positions in the Z axis direction may be stored in advance in the storage unit 27 and the CPU 21 may calculate the position in the Z axis direction with reference to the table. However, the invention is not limited to this example.

In step SP11, the CPU 21 performs the bright point correcting process similarly to the first embodiment, and displays, for example, the positions in the Z axis direction of the bright points BP deformed into a circular shape at the time of displaying the biological sample image on the display unit 26.

Accordingly, the biological sample image acquiring apparatus 1 can provide only the bright points BP based on the colored light emitted from the fluorescent markers EM coupled to a specific gene in a circular shape and can provide the positions in the thickness direction of the bright points BP at the same time.

2-3. Operations and Advantages

According to the above-mentioned configuration, the biological sample image acquiring apparatus 1 moves the focal plane FP of the objective lens 12A in the thickness direction of the biological sample SPL and also accelerates or decelerates the focal plane so that the speed in the in-plane direction varies with the movement in the thickness direction.

The biological sample image acquiring apparatus 1 exposes the imaging device 30 to light to acquire the biological sample image while moving the focal plane FP in the thickness direction of the biological sample SPL and in the in-plane direction thereof.

Therefore, in the biological sample image acquiring apparatus 1, since the bright point BP based on the fluorescent marker EM wobbles due to the movement and becomes thus elliptical, the bright point BP based on the fluorescent marker EM can be distinguished from the bright point BP based on the noise without being affected by the movement on the basis of the shapes.

Accordingly, the biological sample image acquiring apparatus 1 can remove the bright point based on the noise from the acquired biological sample image, thereby improving the detection precision.

When the cell nucleus is stained, the biological sample image acquiring apparatus 1 can extract the bright point BP based on the fluorescent marker EM existing in the cell nucleus by detecting the color component of the neighboring pixels of the bright point BP based on the fluorescent marker EM and determining whether the detected color component is the cell-nucleus staining color component.

Therefore, the biological sample image acquiring apparatus 1 can extract only the bright points BP based on the fluorescent markers EM existing in a cell nucleus and detect the number of bright points BP existing in the cell nucleus with higher precision, for example.

The biological sample image acquiring apparatus 1 accelerates or decelerates the focal plane so that the speed in the in-plane direction varies with the movement in the thickness direction, at the time of moving the focal plane in the in-plane direction. Accordingly, in the biological sample image acquiring apparatus 1, the major/minor axis ratio of the bright point BP varies depending on the position in the thickness direction and it is thus possible to detect the position in the thickness direction of the bright point BP.

Accordingly, the biological sample image acquiring apparatus 1 can detect the position in the thickness direction of the bright point BP even when cell nucleuses overlap in the thickness direction. Therefore, it is possible to determine in which cell nucleus the fluorescent marker EM exists, thereby improving the detection precision.

According to the above-mentioned configuration, the imaging device 30 is exposed to light to acquire the biological sample image while moving the focal plane FP of the objective lens 12A in the thickness direction of the biological sample SPL and moving the relative position between the biological sample SPL and the imaging device 30 in the in-plane direction. Accordingly, since the image based on the movement can be distinguished from the image based on the noise, it is possible to improve the detection precision.

3. Third Embodiment

A third embodiment is different from the first embodiment in the movement control of the movable stage 11 in the data acquiring process. They are different from each other regarding some processes regarding the biological sample in the biological sample image correcting and displaying process. The configuration of the biological sample image acquiring apparatus 1 is similar to that of the first embodiment, and thus the description is not repeated.

3-1. Data Acquiring Process

Similarly to the first embodiment, when an instruction to acquire an image of a fluorescence-stained biological sample is received from the operation input unit 24, the CPU 21 serves as the stage movement controller 41, the biological sample acquiring unit 42, and the data recorder 43.

The stage movement controller 41 moves the movable stage 11 in the Z axis direction at a constant speed so as to get close to the objective lens 12A so that the focal plane FP of the objective lens 12A moves from the cover glass CG side of the biological sample SPL to the slide glass SG side.

At the same time, the stage movement controller 41 moves the movable stage 11 in the X axis direction and the Y axis direction so as to draw a semi-circle at a constant speed in the XY plane while moving the movable stage 11 in the Z axis direction. That is, the stage movement controller 41 moves the movable stage 11 to draw a spiral line in the Z axis direction.

Figure 11:
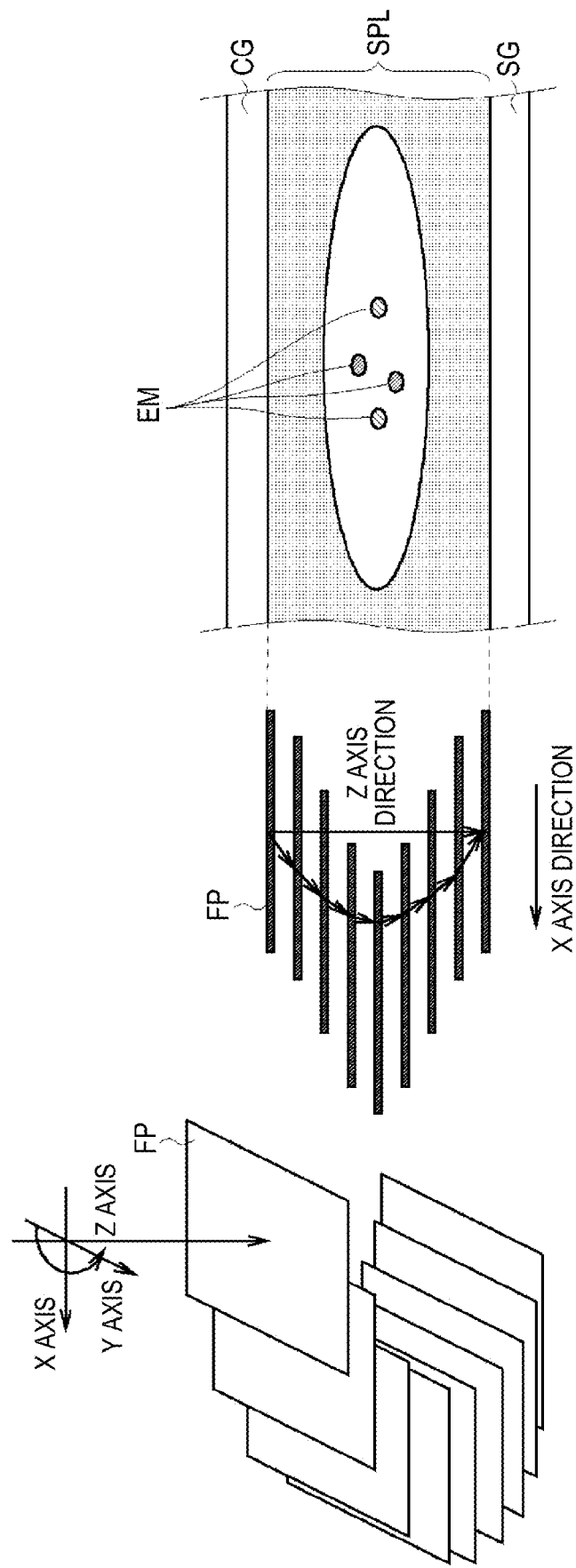
FIG. 11 is a diagram schematically illustrating the movement of the focal plane in the third embodiment.

At this time, as shown in FIG. 11, the focal plane FP of the objective lens 12A is moved at a constant speed in the Z axis direction from the cover glass CG side of the biological sample SPL to the slide glass SG side and is also moved to draw a semi-circle in the XY plane.

Figure 12A:
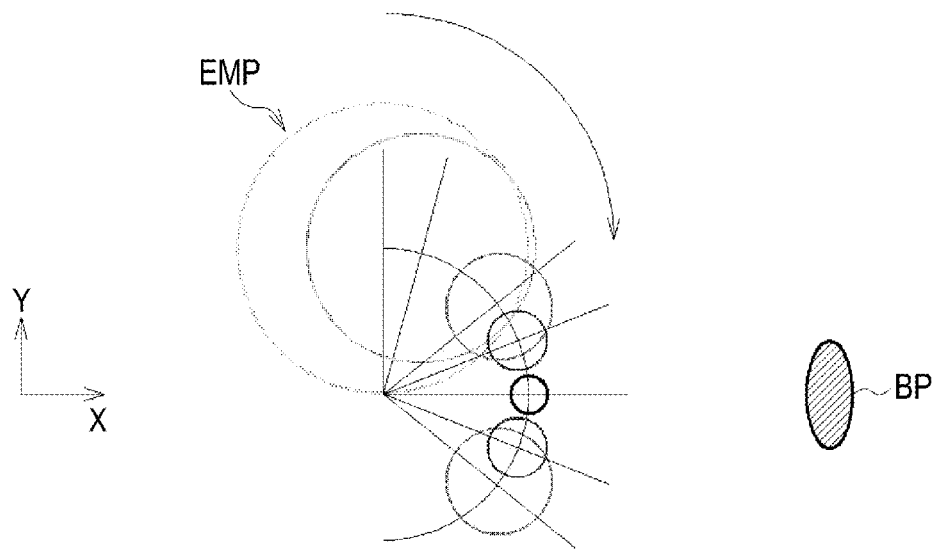
FIGS. 12A and 12B are diagrams schematically illustrating a fluorescent marker image and a bright point in the third embodiment.

Accordingly, the fluorescent marker EM located in the vicinity of the center of the biological sample SPL is imaged by the imaging device 30 so that the fluorescent marker image EMP thereof is almost stopped in the X axis direction and is moved in the Y axis direction as shown in FIG. 12A. Therefore, the fluorescent marker EM appears in the biological sample image as a substantially elliptical bright point BP of which the major axis is directed to the Y axis direction.

Figure 12B:
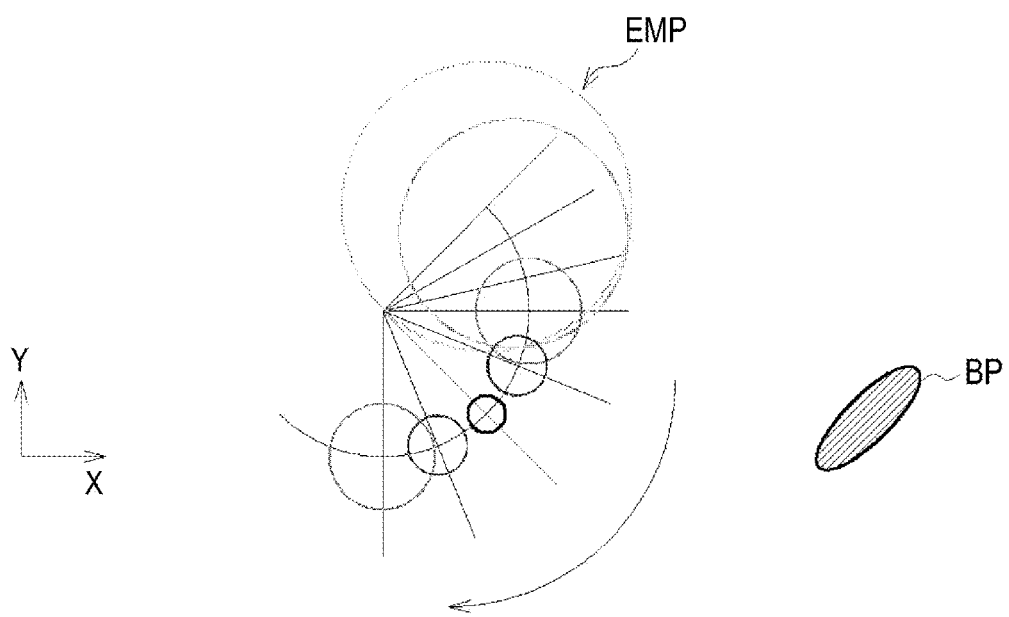

The fluorescent marker EM located close to the slide glass SG is imaged by the imaging device 30 so that the fluorescent marker image EMP thereof is decelerated in the X axis direction and the Y axis direction, as shown in FIG. 12B. Therefore, the fluorescent marker EM appears in the biological sample image as a substantially elliptical bright point BP of which the major axis is inclined about the X axis and the Y axis.

In this way, the fluorescent marker EM appears in the biological sample image as a substantially elliptical bright point BP inclined by an angle corresponding to the position in the Z axis direction.

The biological sample image acquiring unit 42 exposes the imaging device 30 to light to cause the imaging device 30 to image the target sample region while the movable stage 11 is being moved in the Z axis direction and in the in-plane direction by the stage movement controller 41, and connects the resultant images of the sample regions to generate a biological sample image.

When the biological sample image is generated, the data recorder 43 generates sample data including pixel information representing all of the biological sample image or a part capable of reproducing the biological sample image.

The data recorder 43 adds data representing identification information of the biological sample image to the sample data and records the sample data to which the data is added in the memory unit 27.

3-2. Biological Sample Image Correcting Displaying Process

The CPU 21 performs the same process as the first embodiment on the basis of the biological sample image correcting and displaying process (FIG. 11), but calculates the position in the thickness direction of a bright point BP of which the major/minor axis ratio is equal to or greater than a threshold value, for example, between the in-nucleus bright point extracting process and the bright point correcting process.

Specifically, the CPU 21 calculates the angle formed by the major axis of the extracted bright point BP and the X axis and calculates the position in the Z axis direction from a predetermined reference position on the basis of the moving direction in the XY plane of the movable stage 11 moved by the stage movement controller 41. In calculating the position in the Z axis direction, for example, a table in which the angles formed by the major axes of the bright points BP and the X axis are correlated with the positions in the Z axis direction may be stored in advance in the storage unit 27 and the CPU 21 may calculate the position in the Z axis direction with reference to the table. However, the invention is not limited to this example.

In step SP11, the CPU 21 performs the bright point correcting process similarly to the first embodiment, and displays, for example, the positions in the Z axis direction of the bright points BP deformed into a circular shape at the time of displaying the biological sample image on the display unit 26.

Accordingly, the biological sample image acquiring apparatus 1 can provide only the bright points BP based on the colored light emitted from the fluorescent markers EM coupled to a specific gene in a circular shape and can provide the positions in the thickness direction of the bright points BP at the same time.

3-3. Operations and Advantages

According to the above-mentioned configuration, the biological sample image acquiring apparatus 1 moves the focal plane FP of the objective lens 12A in the thickness direction of the biological sample SPL and also moves the focal plane so that the moving direction in the in-plane direction varies with the movement in the thickness direction.

The biological sample image acquiring apparatus 1 exposes the imaging device 30 to light to acquire the biological sample image while moving the focal plane FP in the thickness direction of the biological sample SPL and in the in-plane direction.

Therefore, in the biological sample image acquiring apparatus 1, since the bright point BP based on the fluorescent marker EM wobbles due to the movement and becomes substantially elliptical, the bright point BP based on the fluorescent marker EM can be distinguished from the bright point BP based on the noise without being affected by the movement on the basis of the shapes.

Accordingly, the biological sample image acquiring apparatus 1 can remove the bright point based on the noise from the acquired biological sample image, thereby improving the detection precision.

When the cell nucleus is stained, the biological sample image acquiring apparatus 1 can extract the bright point BP based on the fluorescent marker EM existing in the cell nucleus by detecting the color component of the neighboring pixels of the bright point BP based on the fluorescent marker EM and determining whether the detected color component is the cell-nucleus staining color component.

Therefore, the biological sample image acquiring apparatus 1 can extract only the bright points BP based on the fluorescent markers EM existing in a cell nucleus and detect the number of bright points BP existing in the cell nucleus with higher precision, for example.

The biological sample image acquiring apparatus 1 moves the biological sample SPL and the imaging device 30 in the in-plane direction so that the moving direction in the in-plane direction varies with the movement in the thickness direction, at the time of moving the biological sample SPL and the imaging device 30 in the in-plane direction. Accordingly, in the biological sample image acquiring apparatus 1, the slope of the bright point BP in the in-plane direction varies depending on the position in the thickness direction and it is thus possible to detect the position in the thickness direction of the bright point BP.

Accordingly, the biological sample image acquiring apparatus 1 can detect the position in the thickness direction of the bright point BP even when cell nucleuses overlap in the thickness direction. Therefore, it is possible to determine in which cell nucleus the fluorescent marker EM exists, thereby improving the detection precision.

According to the above-mentioned configuration, the imaging device 30 is exposed to light to acquire the biological sample image while moving the focal plane FP of the objective lens 12A in the thickness direction of the biological sample SPL and moving the relative position between the biological sample SPL and the imaging device 30 in the in-plane direction. Accordingly, since the image based on the movement can be distinguished from the image based on the noise, it is possible to improve the detection precision.

4. Fourth Embodiment

A epidermal growth factor receptor (EGFR) existing through a cell membrane is involved in carcinogenesis due to overexpression, mutation, or the like, growth of cancer, or metabasis of cancer.

Figure 13A:
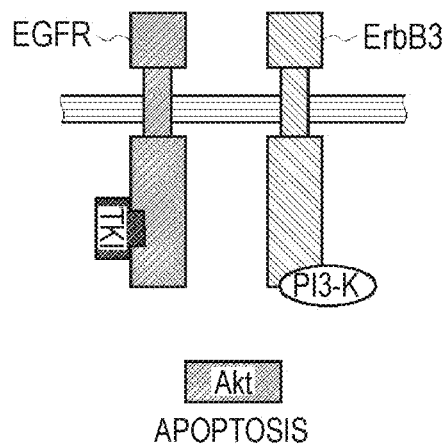
FIGS. 13A to 13E are diagrams schematically illustrating a resistance acquiring model.
Figure 13B:
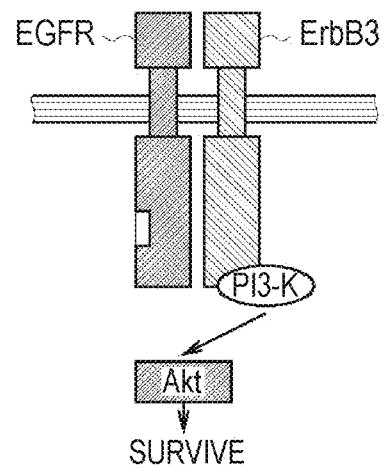

By administering gefitinib or erlotinib which is an EGFR tyrosine kinase inhibitor (EGFR-TKI) to a patient with non-small-cell lung cancer having EGFR mutations, it is known that the signal transmission in the PI3-K/Akt path is inhibited and the cancer cells causes apoptosis to reduce the cancer (FIG. 13A). However, when ErbB3 approaches the EGFR, it is proved that the gefitinib and erlotinib do not work and the cancer cells are left alive (FIG. 13B). (Lynch T. J., et al. "Activating mutations in the epidermal growth factor receptor underlying responsiveness of non-small-cell lung cancer to gefitinib." New England Journal of Medicine, Vol. 350, No. 21, 2004, p.p. 2129-2139.)

Figure 13C:
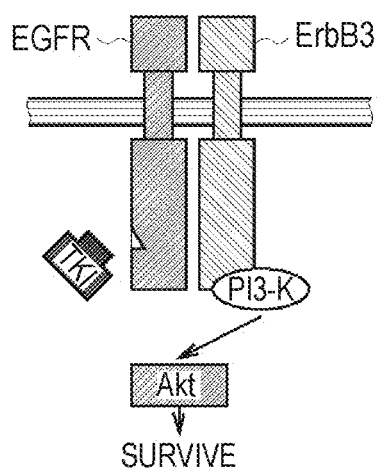

It is also proved that a mutation EGFR having resistance to the gefitinib and erlotinib is expressed (FIG. 13C). (Kobayashi S., et al. "EGFR Mutation and Resistance of Non-Small-Cell Lung Cancer to Gefitinib." New England Journal of Medicine, Vol. 352, No. 21, 2004, p.p. 786-2139.)

Figure 13D:
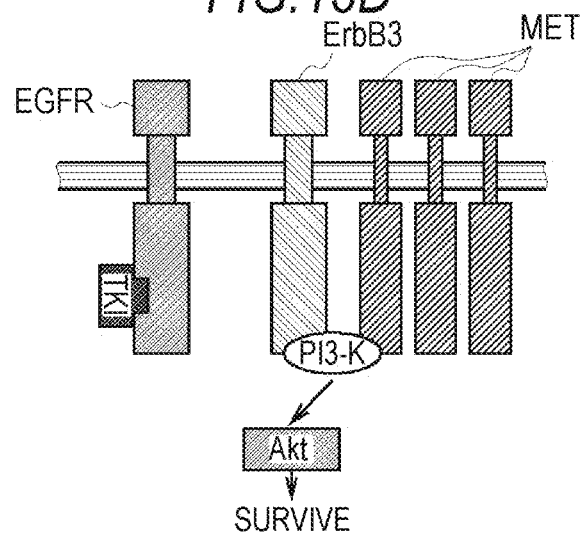

It is also proved that a MET (Mesenchymal-Epithelial Transition Factor) exhibits the resistance to the gefitinib depending on the ErbB3 after the MET is locally amplified in a lung cancer cell line sensitive to gefitinib (FIG. 13D). (Engelman J. A., et al. "MET Amplification Leads to Gefitinib Resistance in Lung Cancer by Activating ERBB3 Signaling." Science, Vol. 361, No. 5827, 2007, p.p. 1039-1043.)

Figure 13E:
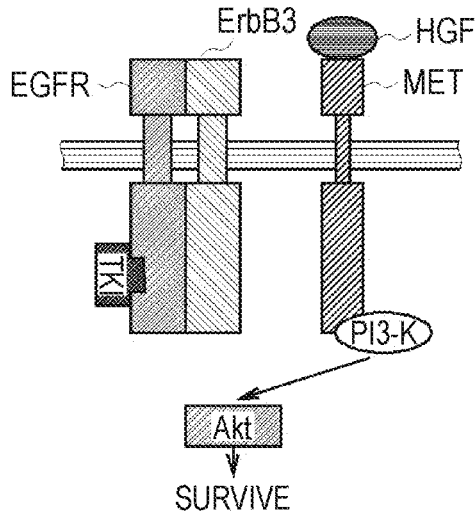

It is also proved that a hepatocyte growth factor (HGF) transmits a signal in the PI3-K/Akt path by the MET, not by the EGFR or the ErbB3 (FIG. 13E). (Yano S., et al. "Hepatocyte Growth Factor Induces Resistance of Lung Adenocarcinoma with Epidermal Growth Factor Receptor-Activating Mutations" New Cancer Research, Vol. 68, No. 22, 2008, p.p. 9479-9487.)

In this way, the effects of medicines or inhibitors may greatly vary depending on the distances between specific proteins or genes, and thus it is very important to accurately measure the distance between the proteins or genes.

In the fourth embodiment, the distance between target proteins or genes is accurately measured. In the fourth embodiment, the acquisition of an image of a biological sample SPL stained with fluorescent markers EM1 and EM2 emitting light (colors) of different wavelengths for different proteins or genes such as EGFR and ErbB3 will be described.

4-1. Configuration of Biological Sample Image Acquiring Apparatus

Figure 14:
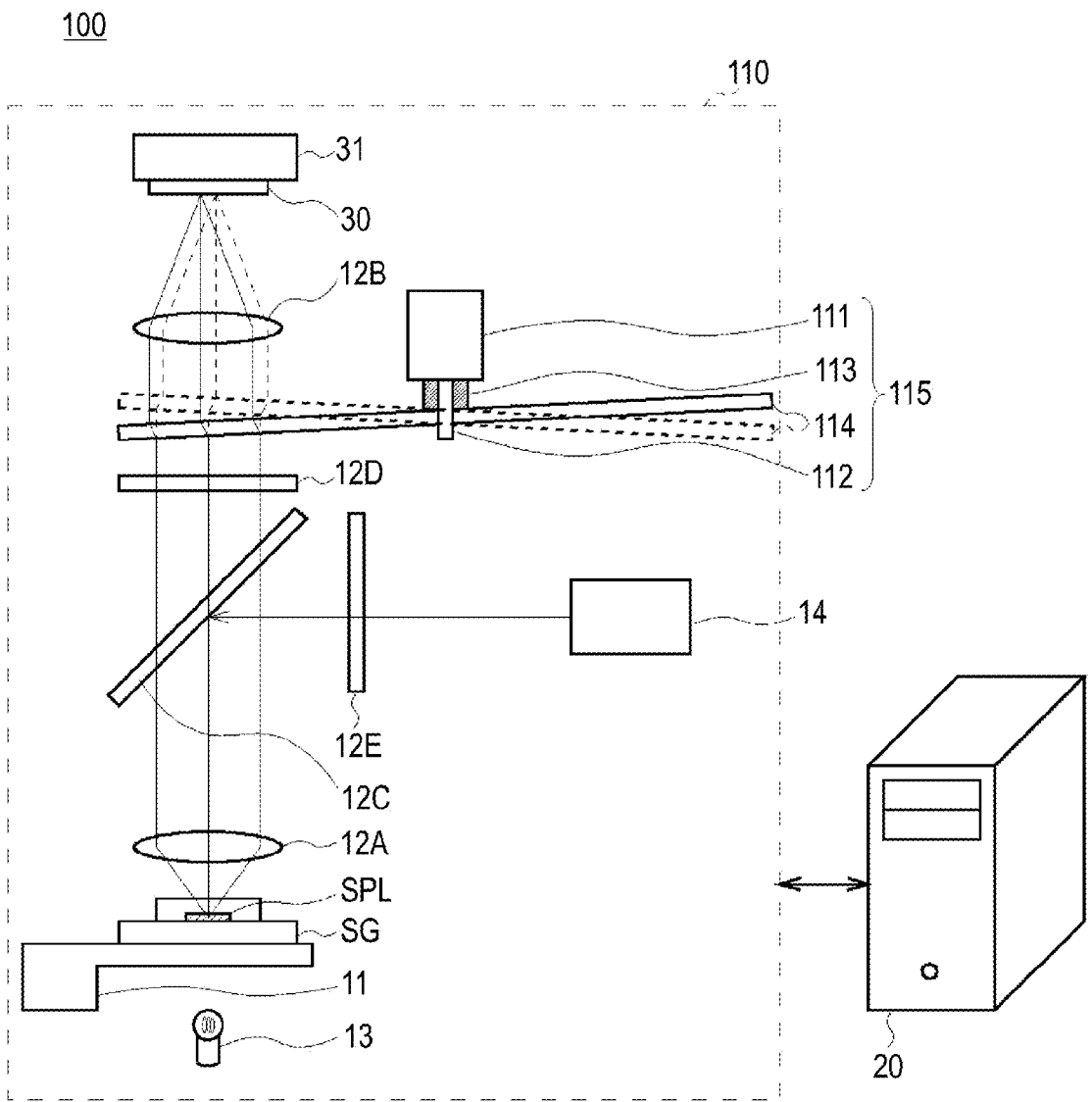
FIG. 14 is a diagram schematically illustrating a biological sample image acquiring apparatus according to a fourth embodiment.

In FIG. 14 in which corresponding elements of FIG. 1 are referenced by like reference numerals and signs, a biological sample image acquiring apparatus 100 according to the fourth embodiment is shown. The biological sample image acquiring apparatus 100 includes a microscope 110 and a data processor 20.

The microscope 110 includes an imaging position moving unit 115 having a motor 111, a rotation shaft 112, an inclination pedestal 113, and a transparent plate 114.

The motor 111 rotates the transparent plate 114 via the rotation shaft 112 under the control of the data processor 20.

The inclination pedestal 113 is disposed around the rotation shaft 112 and inclines the transparent plate 114 at a predetermined inclination angle about the rotation shaft 112.

The transparent plate 114 is formed in a disk shape with a predetermined thickness having a top surface and a bottom surface parallel to each other out of transparent glass or plastic with refractive index different from that of air, and the rotation shaft 112 is inserted into and fixed to the center thereof.

The imaging position moving unit 115 is disposed so that the rotation shaft 112 is parallel to the optical axis between the imaging lens 12B and the emission filter 12D. The imaging position moving unit 115 is fixed to a predetermined position of the microscope 110 so that a part of the transparent plate 114 is located between the imaging lens 12B and the emission filter 12D.

Accordingly, in the microscope 110, when the motor 111 is activated and the transparent plate 114 is rotated with the rotation of the motor 111, the transparent plate 114 moves up and down while changing the angle about the optical axis direction between the imaging lens 12B and the emission filter 12D.

In the microscope 110, when exciting light is applied to a biological sample SPL from the light source 14, colored light is emitted from the fluorescent markers EM1 and EM2 stained on the biological sample SPL. The colored light reaches the transparent plate 114 via the objective lens 12A, the dichroic mirror 12C, and the emission filter 12D.

The colored light reaching the transparent plate 114 is refracted and transmitted by the top surface and the bottom surface of the transparent plate 114 and is concentrated on the imaging device 30 via the imaging lens 12B.

When the transparent plate 114 is being rotated, the colored light reaching the transparent plate 114 varies in refraction direction depending on the inclination angle of the transparent plate 114 between the imaging lens 12B and the emission filter 12D. Accordingly, the optical axis of the colored light passing through the transparent plate 114 is moved to draw a circle about the optical axis before the colored light is incident on the transparent plate 114.

The microscope 110 magnifies the image of the colored light by the use of the objective lens 12A, moves the imaging position by the use of the transparent plate 114, concentrates the image by the use of the imaging lens 12B, and focuses the concentrated image on the imaging plane of the imaging device 30.

4-2. Data Acquiring Process

The CPU 21 receives an instruction to acquire the image of the fluorescence-stained biological sample SPL from the operation input unit 24. At this time, the CPU 21 serves as a stage movement controller 41, a biological sample image acquiring unit 42, a data recorder 43, an imaging position movement controller 44, a distance calculator 45, and a display controller 46 on the basis of the program corresponding to the acquisition instruction, as shown in FIG. 15. The CPU 21 emits exciting light from the light source 14 when the program is executed.

The stage movement controller 41 moves the movable stage 11 so that a target sample region of the biological sample SPL is located in the imaging range AR.

Figure 16A:
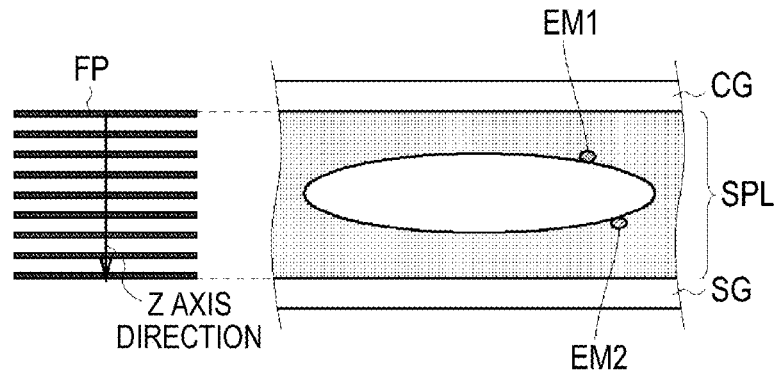
FIGS. 16A, 16B, and 16C are diagrams schematically illustrating movement of a focal plane only in the Z axis direction and a biological sample image and a sharpened image at that time.

As shown in FIG. 16A, the stage movement controller 41 moves the movable stage 11 in the Z axis direction at a constant speed so as to get close to the objective lens 12A so that the focal plane FP of the objective lens 12A moves from the cover glass CG side of the biological sample SPL to the slide glass SG side.

The biological sample image acquiring unit 42 exposes the imaging device 30 to light to cause the imaging device 30 to image the target sample region while moving the movable stage 11 in the Z axis direction by the use of the stage movement controller 41, thereby acquiring the resultant fluorescent image.

Figure 16B:
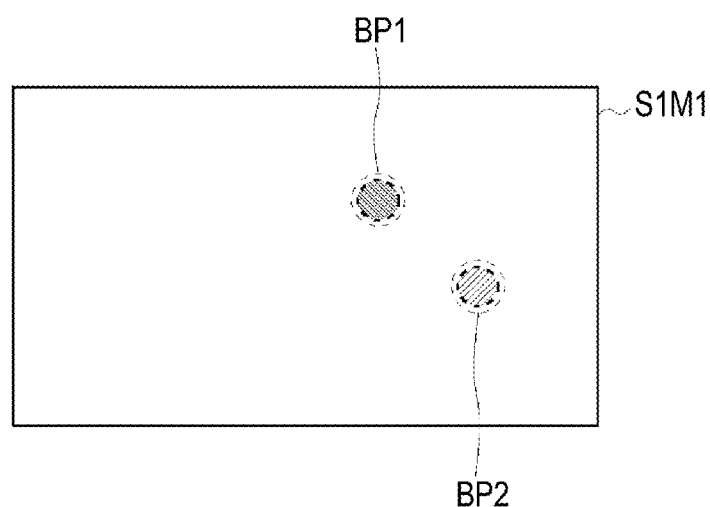

The biological sample image acquiring unit 42 generates a biological sample image SIM1 by sequentially acquiring and connecting the fluorescent images allocated to the imaging ranges AR, as shown in FIG. 16B.

In the acquired biological sample image SIM1, the fluorescent markers EM1 and EM2 stained on the biological sample SPL appear as blurred bright points BP1 and BP2 on the basis of a point spread function (PSF).

The biological sample image acquiring unit 42 basically detects the brightness values of the bright points BP1 and BP2 from the biological sample image SIM1 and calculates the point spread function of the bright points BP1 and BP2. The biological sample image acquiring unit 42 sharpens the bright points BP1 and BP2 using the reversed function of the calculated point spread function (reversed point spread function).

Figure 16C:
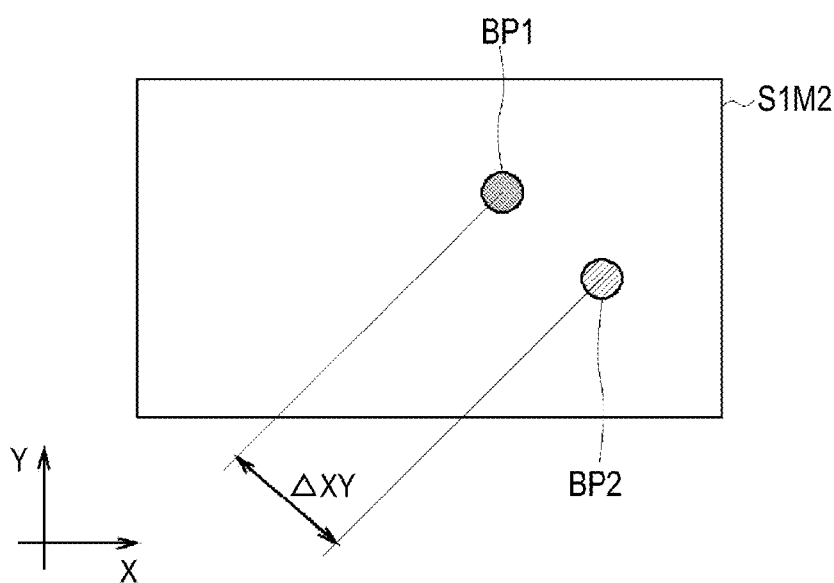

The data recorder 43 stores data of a biological sample image (hereinafter, also referred to as "sharpened image") SIM2 (FIG. 16C) in which the bright points BP1 and BP2 are sharpened as sharpened image data in the storage unit 27.

The stage movement controller 41 moves again the movable stage 11 in the Z axis direction at a constant speed so as to get close to the objective lens 12A so that the focal plane FP of the objective lens 12A moves from the cover glass CG side of the biological sample SPL to the slide glass SG side.

The imaging position movement controller 43 half-rotates the transparent plate 114 via the motor 111 while the focal plane FP is being moved from the cover glass CG side of the biological sample SPL to the slide glass SG side.

Figure 17A:
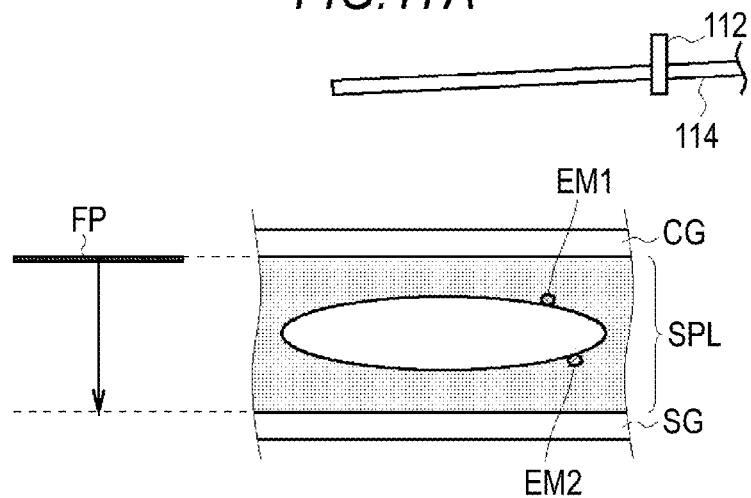
FIGS. 17A, 17B, and 17C are diagrams schematically illustrating movements of a focal plane and a transparent plate.
Figure 17B:
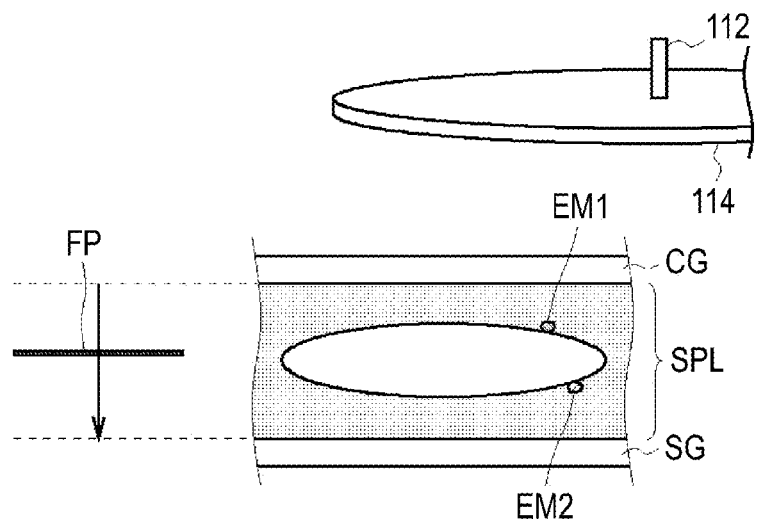
Figure 17C:
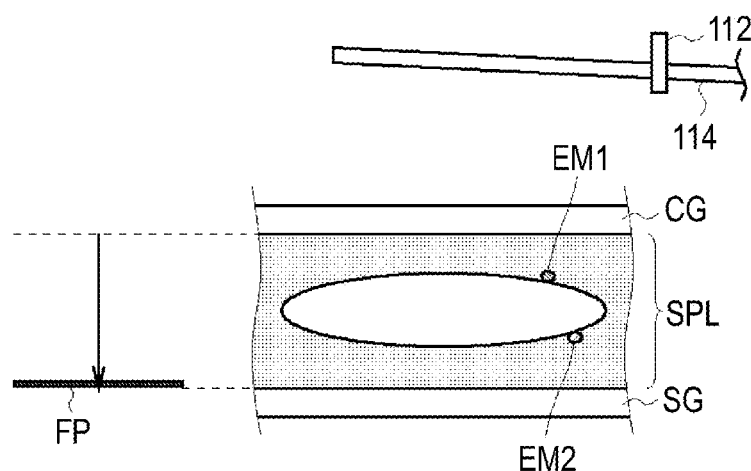

Specifically, in the imaging position movement controller 43, the portion of the transparent plate 114 between the imaging lens 12B and the emission filter 12D is located at the lowest point (FIG. 17A) when the focal plane FP is located on the cover glass CG side as shown in FIGS. 17A to 17C. In FIG. 17A, the configuration other than the rotation shaft 112 and the transparent plate 114 is not shown for the purpose of convenient explanation.

In the imaging position movement controller 43, the transparent plate is rotated so that the portion of the transparent plate 114 between the imaging lens 12B and the emission filter 12D is located in the middle position between the lowest point and the highest point (FIG. 17B) when the focal plane FP is moved to the middle position between the cover glass CG and the slide glass SG.

In the imaging position movement controller 43, the transparent plate is rotated so that the portion of the transparent plate 114 between the imaging lens 12B and the emission filter 12D is located at the highest point (FIG. 17C) when the focal plane FP is moved to the slide glass SG.

Accordingly, the image of the colored light emitted from the fluorescent markers EM1 and EM2 stained on the biological sample SPL is changed in the refraction direction depending on the position of the moving transparent plate 114 and is moved to draw a semi-circle without changing its direction on the imaging plane of the imaging device 30.

The biological sample image acquiring unit 42 exposes the imaging device 30 to light to cause the imaging device 30 to image the target sample region while the movable stage 11 is being moved in the Z axis direction by the use of the stage movement controller 41 and the transparent plate 114 is being half-rotated, thereby acquiring the resultant fluorescent image.

The biological sample image acquiring unit 42 generates a biological sample image (hereinafter, referred to as "elliptical image") EIM (FIG. 18B) by connecting the fluorescent images allocated to the imaging ranges AR. In the elliptical image EIM, the bright point BP appears as an elliptical shape having a slope corresponding to the position in the thickness direction of the biological sample SPL.

The distance calculator 45 reads the sharpened image data stored in the storage unit 27 and extracts the bright points BP1 and BP2 corresponding to the fluorescent markers EM1 and EM2 from the sharpened image SIM2 on the basis of the brightness values.

The distance calculator 45 calculates a distance $\Delta XY$ (FIG. 16C) in the XY plane between the bright points BP1 and BP2 for all the combinations of the bright points BP1 and BP2 appearing in the sharpened image PIM2 on the basis of the imaging magnification power and the pixel size of the imaging device 30.

The distance calculator 45 compares the calculated distance $\Delta XY$ between the bright points BP1 and BP2 with a threshold value and calculates the distance in the Z axis direction so that the bright points BP1 and BP2 are close to each other in the XY plane when the distance $\Delta XY$ is smaller than the threshold value. The threshold value is set to a distance by which it is considered that the fluorescent markers EM1 and EM2 corresponding to the bright points BP1 and BP2 exist in the same cell or a distance by which predetermined effects of medicines or inhibitors are exhibited.

The distance calculator 45 extracts the bright points BP3 and BP4 corresponding to the fluorescent markers EM1 and EM2 as elliptical shapes from the elliptical image EIM (FIG. 18B) on the basis of the brightness values and calculates the angles θ1 and θ2 formed by the major axes of the elliptical shapes of the extracted bright points BP3 and BP4 and the X axis. In addition, the bright point BP1 of the sharpened image SIM2 and the bright point BP3 of the elliptical image EIM are images of the colored light emitted from the same fluorescent marker EM1 and the bright points BP2 and BP4 are images of the colored light emitted from the same fluorescent marker EM2.

The distance calculator 45 calculates the distance $\Delta Z$ in the Z axis direction of the fluorescent markers EM1 and EM2 corresponding to the bright points BP3 and BP4 for the combination of the bright points BP3 and BP4 having the distance $\Delta XY$ in the XY plane smaller than the threshold value using the calculated angles θ1 and θ2, by the use of the following expression.

$$\Delta Z = \frac{Zr \times (\theta 1 - \theta 2)}{2\pi} \quad (1)$$

Here, Zr represents the moving distance by which the movable stage 11 is moved in the Z axis direction while the transparent plate 114 rotates by one turn.

For example, when the difference between the angles θ1 and θ2 set to half-rotate the transparent plate 114 while the movable stage 11 is moved in the Z axis direction by 4 μm is, for example, 0.5π rad, the distance $\Delta Z$ in the Z axis direction between the fluorescent markers EM1 and EM2 is 2 μm.

The distance calculator 45 calculates the actual distance $\Delta$ between the fluorescent markers EM1 and EM2 using the distance $\Delta Z$ in the Z axis direction and the distance $\Delta XY$ in the XY plane between the fluorescent markers EM1 and EM2, by the use of the following expression.

$$\Delta = (\Delta XY^2 + \Delta Z^2)^{0.5} \quad (2)$$

The data recorder 43 correlates the sharpened image data as the data of the sharpened image SIM2 with the information (hereinafter, also referred to as "spacing information") on the actual distance $\Delta$ between the fluorescent markers EM1 and EM2 and stores the resultant data in the storage unit 27.

When an instruction to display the sharpened image SIM2 is received from the operation input unit 24, the display controller 46 reads the sharpened image data and the spacing information correlated with the sharpened image data from the storage unit 27.

The display controller 46 adds the actual distance $\Delta$ based on the spacing information between the bright points BP1 and BP2 corresponding to the fluorescent markers EM1 and EM2 to the sharpened image SIM2 of the read sharpened image data and displays the resultant on the display unit 26.

4-3. Data Acquiring Process

Figure 19:
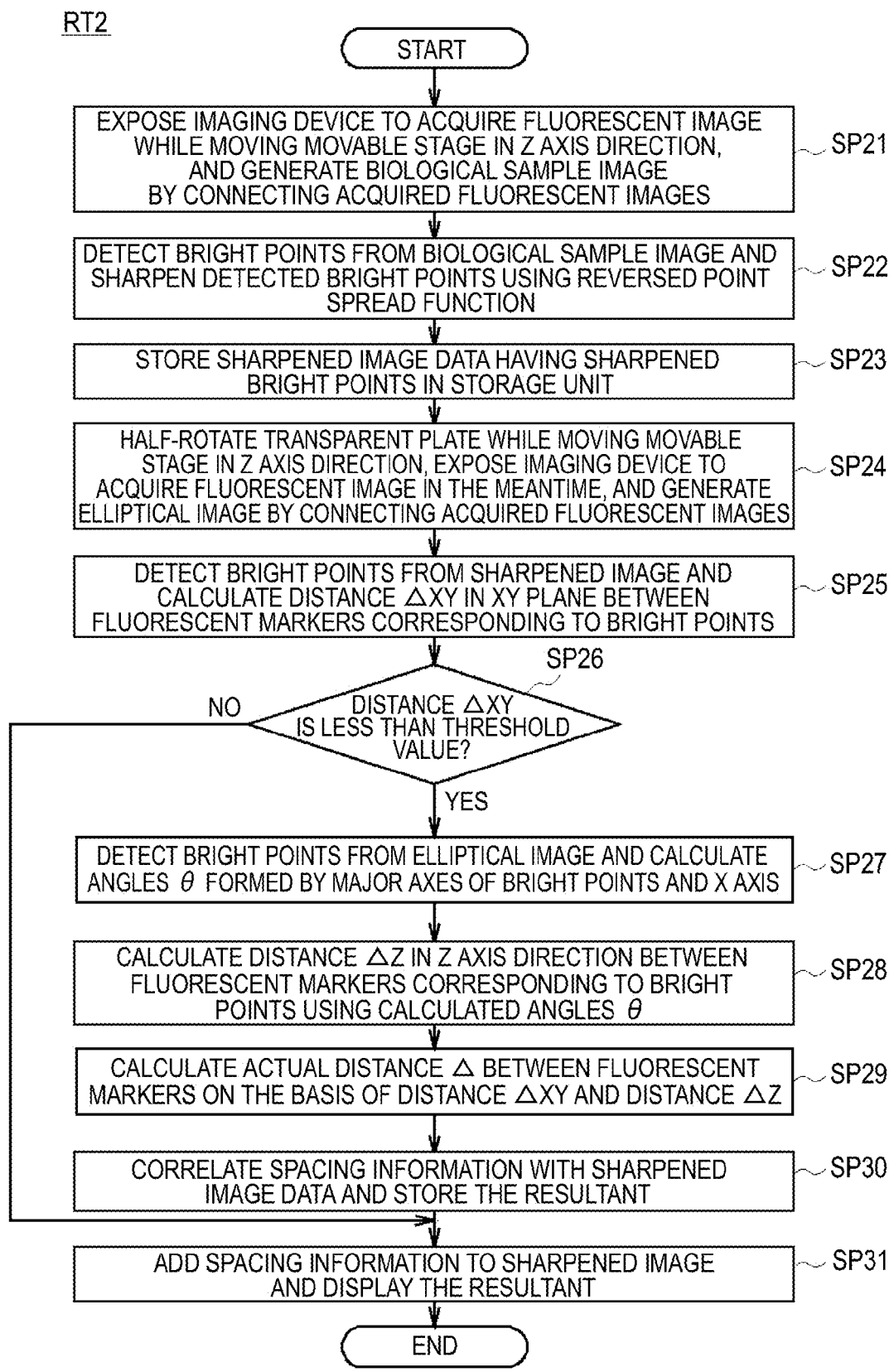
FIG. 19 is a flowchart illustrating a data acquiring procedure.

The above-mentioned data acquiring process will be described with reference to the flowchart shown in FIG. 19.

In practice, when routine RT2 is started, the CPU 21 performs the process of step SP21. In step SP21, the CPU 21 moves the movable stage 11 in the Z axis direction at a constant speed so that the focal plane FP is moved from the cover glass CG side of the biological sample SPL to the slide glass SG side. The CPU 21 exposes the imaging device 30 to light to acquire a fluorescent image while the movable stage 11 is being moved, generates the biological sample image SIM1 by connecting the fluorescent images of the sample regions allocated to the imaging ranges AR, and then performs the process of step SP22.

In step SP22, the CPU 21 detects the bright points BP1 and BP2 from the biological sample image SIM1 and sharpens the bright points BP1 and BP2 using the reversed point spread function. In step SP23, the CPU 21 stores the sharpened image data of the sharpened image SIM2 in which the bright points BP1 and BP2 are sharpened in the storage unit 27 and then performs the process of step SP24.

In step SP24, the CPU 21 moves the movable stage 11 in the Z axis direction at a constant speed so that the focal plane FP is moved from the cover glass CG side of the biological sample SPL to the slide glass SG side, and half-rotates the transparent plate 114 at the same time. The CPU 21 exposes the imaging device 30 to light to acquire the fluorescent image while the movable stage 11 is being moved, generates the elliptical image EIM by connecting the fluorescent images of the sample regions allocated to the imaging ranges AR, and then performs the process of step SP25.

In step SP25, the CPU 21 detects the bright points BP1 and BP2 from the sharpened image SIM2 and calculates the distance $\Delta XY$ in the XY plane between the bright points BP1 and BP2. In step SP26, the CPU 21 determines whether the distance $\Delta XY$ is less than the threshold value, and then performs the process of step SP27 when the determination result is YES.

On the other hand, when the determination result in step SP26 is NO, it means that the pair of fluorescent markers EM1 and EM2 having a distance smaller than the distance set as the threshold value do not exist, and then the CPU 21 performs the process of step SP31.

In step SP27, the CPU 21 detects the bright points BP3 and BP4 corresponding to the fluorescent markers EM1 and EM2 determined to have a distance $\Delta XY$ less than the threshold value in step SP25 from the elliptical image EIM. Then, the CPU 21 calculates the angles $\theta 1$ and $\theta 2$ formed by the major axes of the detected elliptical bright points BP3 and BP4 and the X axis direction and then performs the process of step SP28.

In step SP28, the CPU 21 calculates the distance $\Delta Z$ in the Z axis direction between the fluorescent markers EM1 and EM2 corresponding to the bright points BP3 and BP4 by substituting the calculated angles $\theta 1$ and $\theta 2$ into Expression (1), and then performs the process of step SP29.

In step SP29, the CPU 21 calculates the actual distance $\Delta$ between the fluorescent markers EM1 and EM2 by substituting the distance $\Delta XY$ calculated in step SP25 and the distance $\Delta Z$ calculated in step SP28 into Expression (2), and then performs the process of step SP30.

In step SP30, the CPU 21 correlates the calculated actual distance $\Delta$ between the fluorescent markers EM1 and EM2 as the spacing information with the sharpened image data, stores the resultant data, and then performs the process of step SP31.

In step SP31, the CPU 21 reads the sharpened image data and the spacing information from the storage unit 27 when an instruction to display the sharpened image SIM2 is received from the operation input unit 24. Then, the CPU 21 adds the actual distance $\Delta$ based on the spacing information between the bright points BP1 and BP2 corresponding to the fluorescent markers EM1 and EM2 to the sharpened image SIM2, displays the resultant on the display unit 26, and then ends the flow of the process.

4-4. Operations and Advantages

According to the above-mentioned configuration, the biological sample image acquiring apparatus 100 is provided with the imaging position moving unit 115 circularly moving the image of the biological sample SPL relative to the imaging device 30 without changing the direction.

In the imaging position moving unit 115, the transparent plate 114 is fixed to the rotation shaft 112, which is disposed to be parallel to the optical axis between the objective lens 12A and the imaging device 30 and is rotated by the motor 111, so as to be inclined about the rotation shaft by a predetermined angle.

The transparent plate 114 is partially located between the imaging lens 12B and the emission filter 12D. Accordingly, when the transparent plate 114 is rotated via the rotation shaft 112 by the motor 111, the image of the biological sample SPL magnified by the objective lens 12A is circularly moved in the imaging plane of the imaging device 30 without changing the direction.

The biological sample image acquiring apparatus 100 rotates the transparent plate 114 while moving the movable stage 11 in the Z axis direction and acquires the elliptical image EIM by exposing the imaging device 30 in the meantime.

Figure 20A:
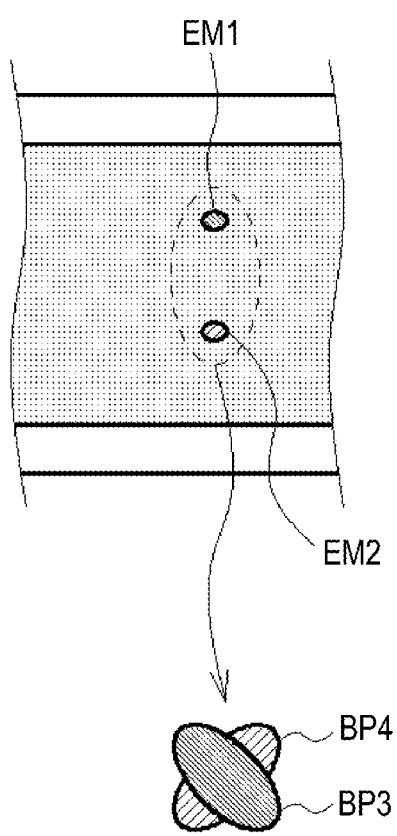
FIGS. 20A and 20B are diagrams schematically illustrating bright points of fluorescent markers separated in the Z axis direction.
Figure 20B:
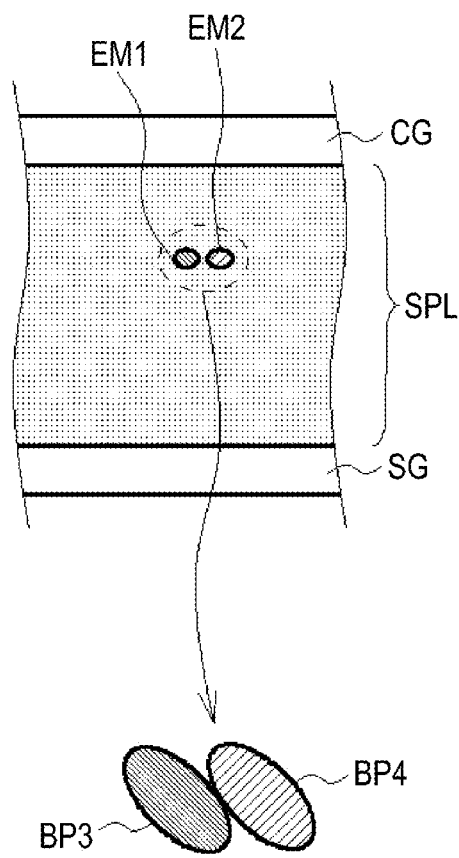

Therefore, in the elliptical image EIM acquired by the biological sample image acquiring apparatus 100, the slopes of the corresponding bright points BP3 and BP4 are greatly different from each other when the fluorescent markers EM1 and EM2 are close to each other in the XY plane but are separated in the Z axis direction as shown in FIG. 20A. On the other hand, when the fluorescent markers EM1 and EM2 are close to each other in the XY plane and are also close to each other in the Z axis direction as shown in FIG. 20B, the slopes of the corresponding bright points BP3 and BP4 are almost the same.

In this way, the biological sample image acquiring apparatus 100 can acquire the elliptical image EIM in which the slope of the bright point BP appearing as a substantially elliptical shape varies depending on the position of the fluorescent marker EM in the thickness direction (in the Z axis direction) in the biological sample SPL.

Accordingly, the biological sample image acquiring apparatus 100 can detect the three-dimensional position of the fluorescent markers EM in the biological sample SPL by detecting the position in the Z axis direction from the slopes of the bright points BP appearing in a substantially elliptical shape, thereby further improving the detection precision.

In the biological sample image acquiring apparatus 100, similarly to the third embodiment, it is possible to facilitate control simply by rotating the transparent plate 114 while moving the movable stage 11 in the Z axis direction, compared with the case where the movable stage 11 is moved in the XY plane while moving the movable stage in the Z axis direction.

In the biological sample image acquiring apparatus 100, the distance $\Delta XY$ in the XY plane between the bright points BP1 and BP2 is calculated from the sharpened image PIM2 by exposing the imaging device 30 to light while moving the movable stage 11 in the Z axis direction.

In the biological sample image acquiring apparatus 100, the distance $\Delta Z$ in the Z axis direction between the bright point BP3 and BP4 is calculated from the elliptical image EIM imaged by rotating the transparent plate 114 while moving the movable stage 11 in the Z axis direction and exposing the imaging device 30 in the meantime.

In the biological sample image acquiring apparatus 100, the actual distance $\Delta$ between the fluorescent markers EM1 and EM2 marked in target proteins or genes is calculated from the calculated distances $\Delta XY$ and $\Delta Z$.

Accordingly, it is possible for the biological sample image acquiring apparatus 100 to accurately measure the distance between the target proteins or genes.

According to the above-mentioned configuration, the image of the biological sample SPL is circularly moved in the imaging plane of the imaging device 30 without changing the direction at the same time of moving the focal plane FP of the objective lens 12A in the thickness direction of the biological sample SPL, and the imaging device 30 is exposed to light in the meantime to acquire the biological sample image (elliptical image EIM). Accordingly, since the distance between the fluorescent markers EM marked on the target proteins or genes can be accurately measured, it is possible to improve the detection precision.

5. Other Embodiments

In the first to fourth embodiments, the focal plane FP is moved in the Z axis direction relative to the biological sample SPL by moving the movable stage 11 in the Z axis direction. The invention is not limited to the configuration, but the focal plane FP may be moved in the Z axis direction relative to the biological sample SPL, for example, by providing a moving mechanism for moving the objective lens 12A in the Z axis direction and moving the objective lens 12A in the Z axis direction.

In the first to third embodiments, the focal plane FP is moved in the in-plane direction by moving the movable stage 11 in the in-plane direction of the XY plane. The invention is not limited to this configuration, the relative position of the biological sample SPL and the imaging device 30 may be moved in the in-plane direction by providing a stage for moving the imaging device 30 in the in-plane direction of the XY plane and moving the imaging device 30 in the in-plane direction by the use of the stage.

In the first to third embodiments, the biological sample image imaged by the imaging device 30 is stored as sample data without any change. The invention is not limited to this configuration, but the biological sample image imaged by the imaging device 30 may be subjected to the in-nucleus bright point extracting process and the bright point correcting process and may then be stored as sample data.

In the second and third embodiments, the positions in the thickness direction of the bright points BP in the biological sample image imaged by the imaging device 30 are calculated in the biological sample image correcting and displaying process. The invention is not limited to this configuration, but the positions in the thickness direction of the bright points BP in the biological sample image imaged by the imaging device 30 in the data acquiring process may be calculated and the bright points BP and the positions in the thickness direction may be correlated and stored as identification information.

In the first embodiment, the major/minor axis ratio of the bright points BP appearing in the biological sample image is set, for example, to 1.43. The invention is not limited to this configuration, but the movable stage 11 may be moved in the Z axis direction and in the in-plane direction so that the major/minor axis ratio of the bright points BP is set to the range of 1.3 to 1.5 in the first and third embodiments. In the second embodiment, the movable stage 11 may be moved so that the moving speed in the in-plane direction varies in the range where the major/minor axis ratio of the bright points BP is 1.3 to 1.5.

In the first and second embodiments, the movable stage 11 is moved in the X axis direction as the in-plane direction. The invention is not limited to this configuration, but the in-plane direction may be the Y axis direction or a direction having a predetermined slope about the X axis or the Y axis as long as it is constant as the in-plane direction.

In the first to fourth embodiments, two objective lenses 12A and 12B are disposed. The invention is not limited to this configuration, but the number of objective lenses may be one. In addition, the magnification powers of the objective lenses 12A and 12B may be changed by the use of a revolver or the like.

In the first to fourth embodiments, the sample data acquired in the biological sample image acquiring process is stored in the storage unit 27. The storage unit 27 is not necessarily disposed inside the data processor 20, but may be disposed outside the data processor 20. The data communication medium with the storage unit 27 is not limited to the bus 28, but may employ a wired or wireless communication medium such as a local area network, the Internet, or a digital satellite broadcast.

In the fourth embodiment, the image of the biological sample SPL formed on the imaging device 30 is circularly moved without changing the slope by rotating the transparent plate 114. The invention is not limited to this configuration, but the image of the biological sample SPL formed on the imaging device 30 may be circularly moved without changing the slope by moving the emission filter 12D.

Figure 21:
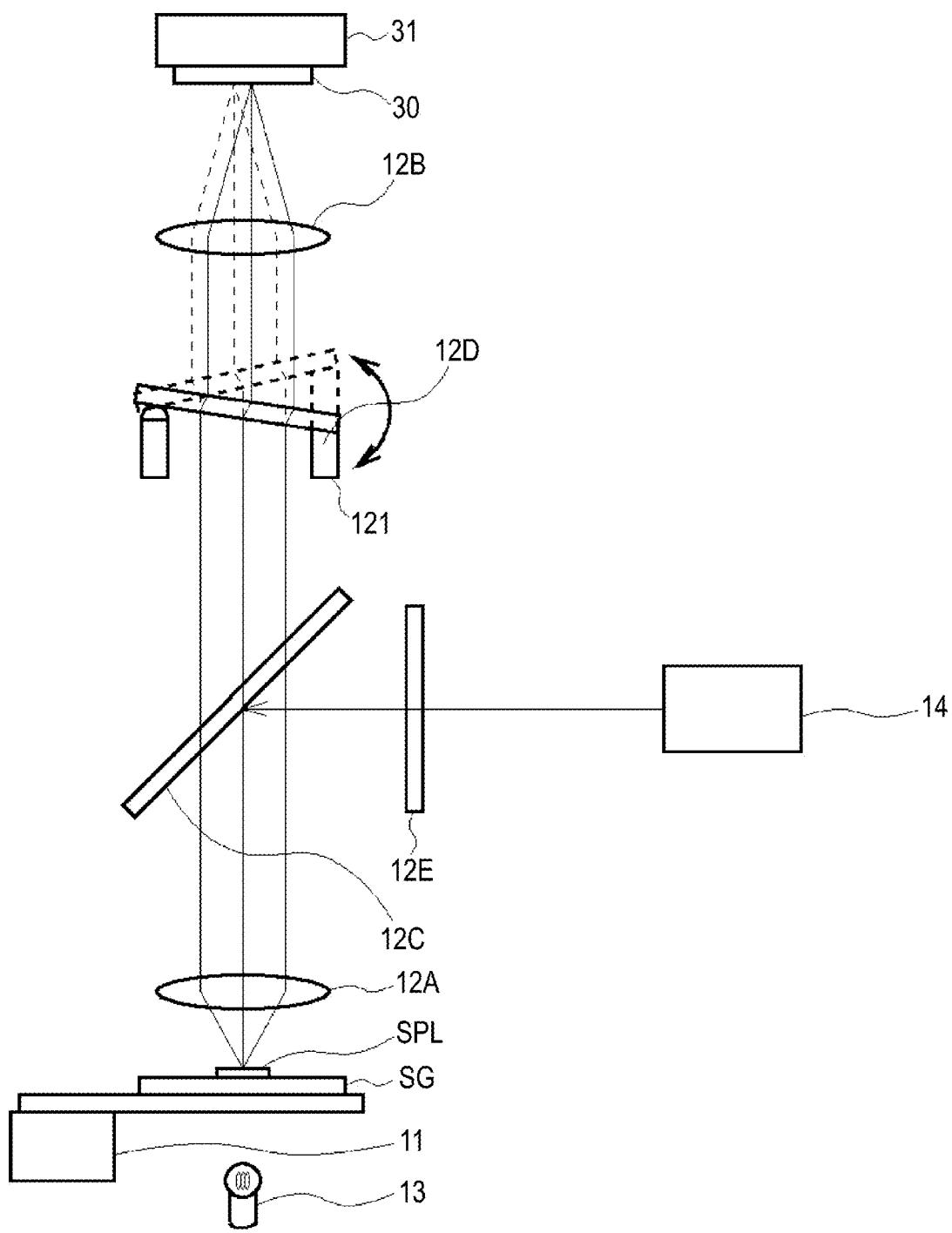
FIG. 21 is a diagram schematically illustrating a biological sample image acquiring apparatus according to another embodiment.

Specifically, as shown in FIG. 21 in which elements corresponding to those of FIG. 14 are referenced by like reference numerals and signs, a biological sample image acquiring apparatus 120 includes an imaging position moving unit 121 moving the imaging position of the image formed on the imaging device 30 by moving the emission filter 12D.

The imaging position moving unit 121 includes a holding portion 122, a support portion 123, actuators 124 and 125, and springs 126 and 127, as shown in FIG. 22.

The holding portion 122 is formed in a flat rectangular shape holding the emission filter 12D and is supported by the supporting portion 123 supporting an end thereof. In the holding portion 122, the actuators 124 and 125 are disposed in two corners neighboring the end supported by the support portion 123. In the holding portion 122, the springs 126 and 127 are disposed at the centers of the sides connecting the ends supported by the support portion 123 and the actuators 124 and 125.

The actuators 124 and 125 are moved up and down under the control of the imaging position movement controller 43 of the data processor 20 to move the emission filter 12D via the holding portion 124.

Each of the springs 126 and 127 has one end connected to the holding portion 122 and the other end fixed to a predetermined position, and urges the emission filter 12D in the Z axis direction via the holding portion 122 with an urging force.

The CPU 21 controls the stage movement controller 41 to move the movable stage 11 in the Z axis direction at a constant speed so that the focal plane FP is moved from the cover glass CG side of the biological sample SPL to the slide glass SG side at the time of acquiring the elliptical image EIM.

The imaging position movement controller 43 moves the actuators 124 and 125 by the use of the following function so as to half-rotate the image formed on the imaging device 30 without changing the slope while moving the movable stage 11.

$$Z1 = A \sin \omega T, Z2 = A \cos \omega T \qquad (3)$$

Here, Z1 represents the position in the Z axis direction of the corner supported by the actuator 124, Z2 represents the position in the Z axis direction of the corner supported by the actuator 125, A represents the amplitude, $\omega$ represents the angular velocity, and T represents the time. The amplitude A, the angular velocity $\omega$, the phase difference between Z1 and Z2 are properly set.

The biological sample image acquiring apparatus 120 can acquire an elliptical image EIM in which the angle of the bright point BP having a substantially elliptical shape varies depending on the position in the Z axis direction of the corresponding fluorescent marker EM in the biological sample SPL, similarly to the elliptical image EIM acquired by the biological sample image acquiring apparatus 100.

In the microscope, the dichroic mirror 12C, the emission filter 12D, and the excitation filter 12E can be replaced as a unit. Accordingly, simply by replacing the unit in the microscope with a unit including the emission filter 12D having the imaging position moving unit 121, it is possible to acquire the elliptical image EIM.

In the third embodiment, the movable stage 11 is moved to draw a semi-circle in the XY plane while moving the movable stage 11 in the Z axis direction at a constant speed and the imaging device 30 is exposed to light to acquire the biological sample image in the meantime. The elliptical bright points BP are extracted from the acquired biological sample image, the angles formed by the major axes of the extracted bright points BP and the X axis are calculated, and the positions in the Z axis direction are calculated on the basis of the calculated angles. The invention is not limited to this configuration.

Figure 23:
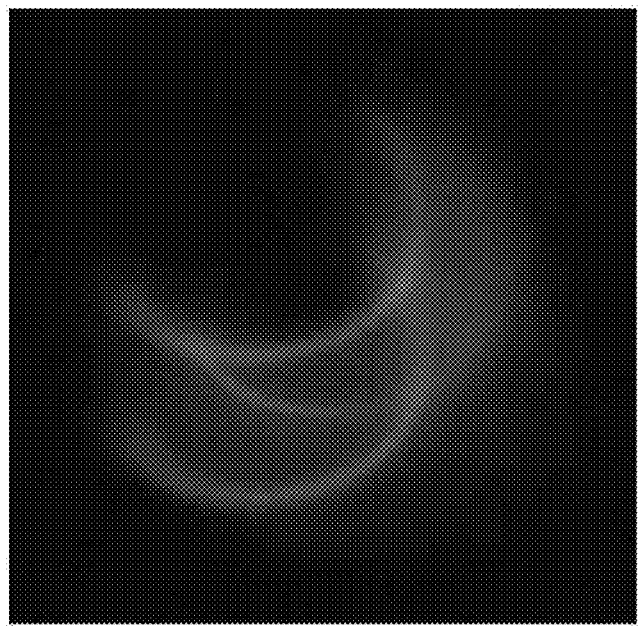
FIG. 23 is a diagram schematically illustrating a biological sample image in which a fluorescent marker appears as a circular-arc image.

For example, in the biological sample image imaged by the imaging device 30 exposed to light while moving the movable stage 11 in the Z axis direction at a constant speed and circularly moving the movable stage 11 in the XY plane at the same time, the fluorescent marker EM may appear as a circular-arc bright point, as shown in FIG. 23.

In this case, the position having the highest brightness level in the circular arc is the position where the objective lens 12A is focused on the fluorescent marker EM. Accordingly, the CPU 21 extracts the circular-arc image in the biological sample image as a bright point and calculates a straight line connecting the middle point of the straight line, which connects both ends of the circular-arc in the bright point, and the middle point of the circular arc.

Then, the CPU 21 calculates the angle formed by the calculated straight line and the X axis and calculates the position in the Z axis direction of the fluorescent marker EM on the basis of the calculated angle.

In this way, in the biological sample image acquiring apparatus 1, when the fluorescent marker EM appears as a circular-arc image in the biological sample image, the brightness level distribution of the circular-arc image varies depending on the position in the thickness direction. Accordingly, it is possible to detect the position in the thickness direction of the fluorescent marker EM from the circular-arc image.

Figure 24:
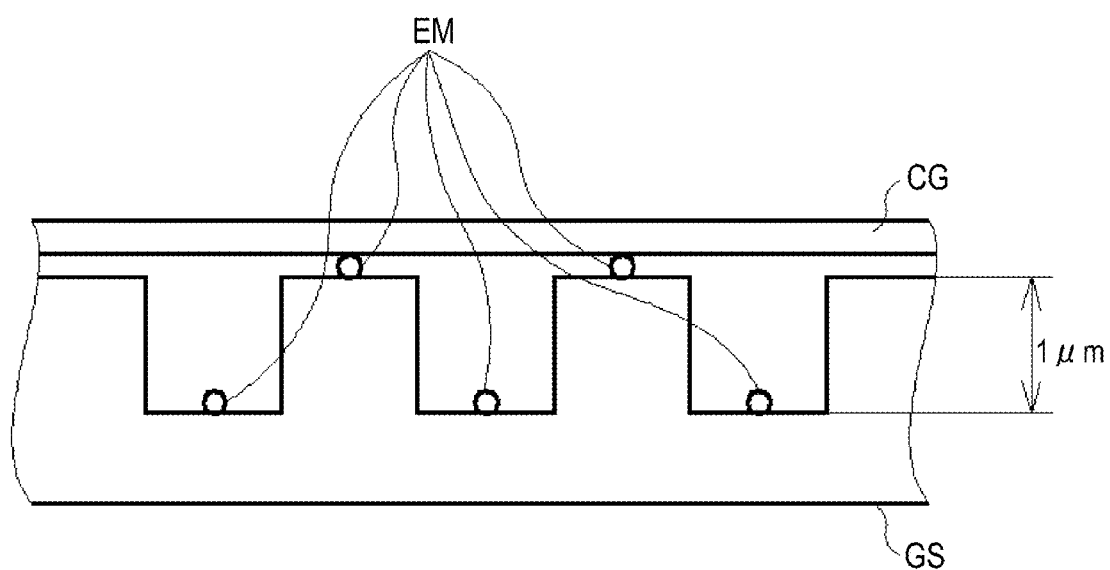
FIG. 24 is a diagram schematically illustrating a test sample.

Here, as shown in FIG. 24, the test result obtained by measuring the distance in the Z axis direction of the fluorescent markers EM disposed on the top and the bottom of a groove, using a sample in which the fluorescent markers EM are disposed on the top and the bottom of the groove of a glass base GS having a groove with a depth of 1 μm, is shown.

In this test, the movable stage having the sample placed thereon is circularly moved in the XY plane at a speed at which it turns in a circle with a radius of 8 μm by one turn per 36 seconds (the angular velocity of 10 deg/s) while it is being moved in the Z axis direction at a speed of 0.23 μm/s. The exposure time of the imaging device is set to 30 s.

Figure 25:
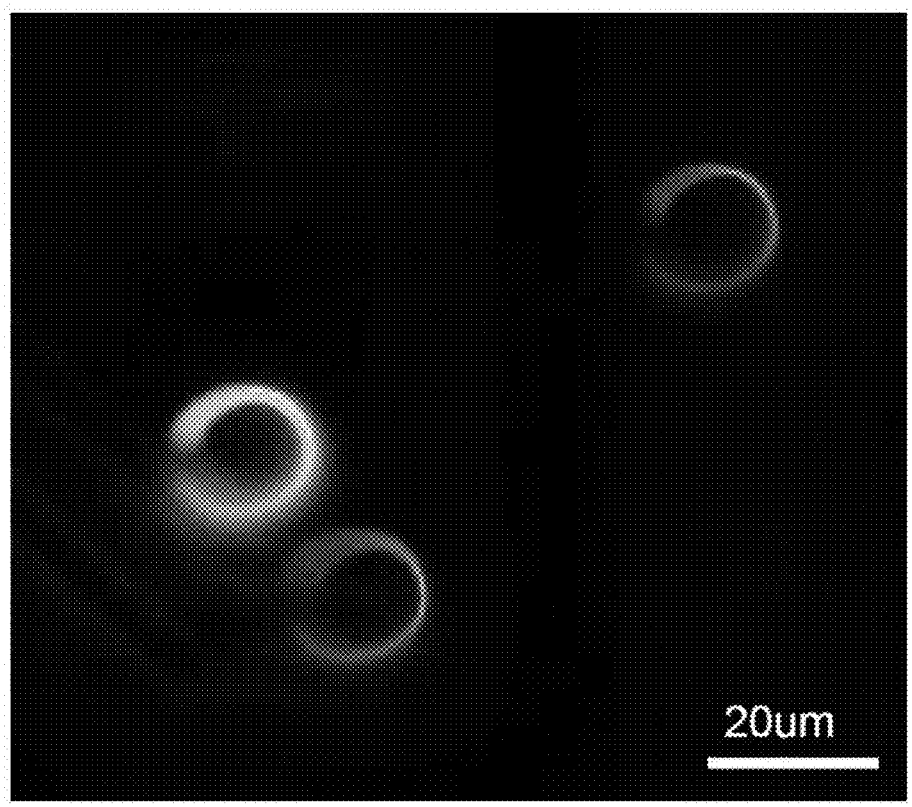
FIG. 25 is a diagram schematically illustrating a sample image.

In the sample image acquired in this test and shown in FIG. 25, the angle difference between the angle of the bright point of the fluorescent marker EM disposed on the top of the groove and the angle of the bright point of the fluorescent marker EM disposed on the bottom thereof is 44.5 deg.

The angle difference of 44.5 deg corresponds to the time difference of 4.45 s, since the stage is moved at the angular velocity of 10 deg/s. Since the focal plane is moved in the Z axis direction at the speed of 0.23 m/s, the time difference of 4.45 s corresponds to 1.04 μm.

Therefore, the distance in the Z axis direction between the fluorescent markers EM disposed on the top and the bottom of the groove is calculated as 1.04 μm Accordingly, the accuracy of this calculation method is proven.

In addition, even when the fluorescent marker EM appears as a circular-arc image in the biological sample image, the elliptical image can be extracted by extracting only the part having a high brightness level. Accordingly, it is possible to calculate the position in the Z axis direction from the elliptical image.

In the fourth embodiment, when the fluorescent marker EM appears as a circular-arc image in the biological sample image, this method can be used.

When the position in the Z axis direction is calculated from the circular-arc image, it is possible to calculate the position in the Z axis direction of the fluorescent marker EM with higher precision by using the biological sample image imaged by moving the movable stage 11 only in the Z axis direction.

Figure 26A:
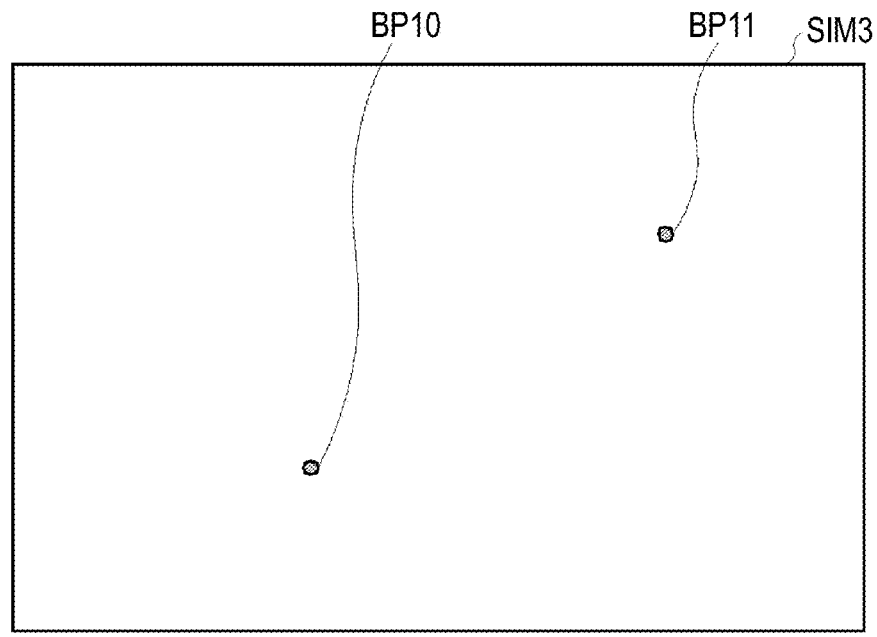
FIGS. 26A and 26B are diagrams schematically illustrating a biological sample image acquired when a movable stage is moved only in the Z axis direction and a biological sample image acquired when the movable stage is circularly moved in the XY plane while being moved in the Z axis direction.

Specifically, the stage movement controller 41 moves the movable stage 11 only in the Z axis direction. The biological sample image acquiring unit 42 exposes the imaging device 30 to light to acquire a biological sample image SIM3 shown in FIG. 26A while the movable stage 11 is being moved.

Figure 26B:
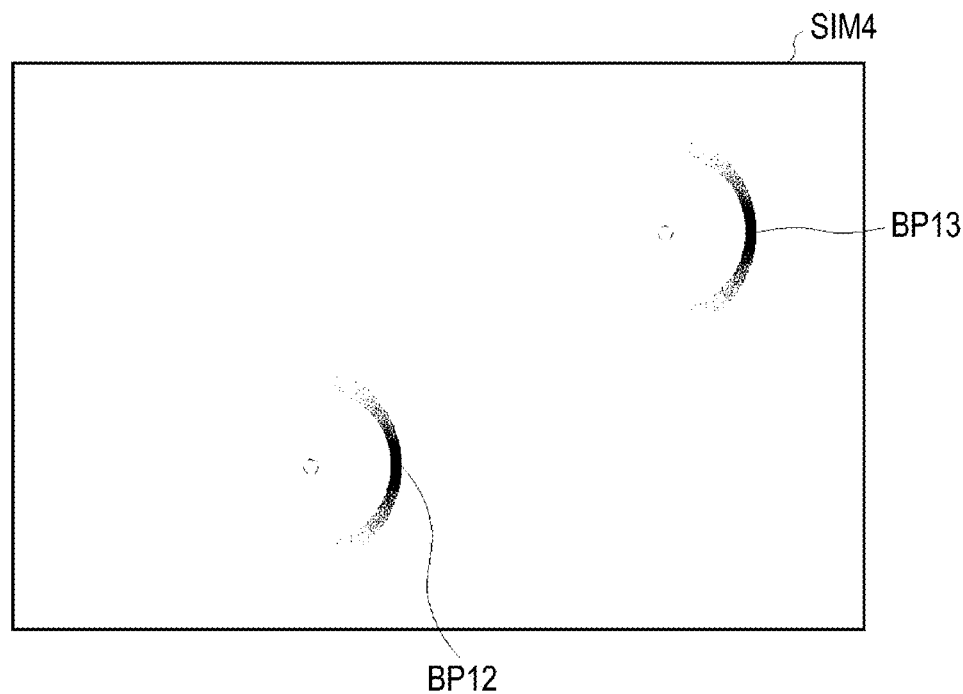

The stage movement controller 41 moves the movable stage 11 to draw a semi-circle about a reference position in the XY plane while moving the movable stage in the Z axis direction using as a reference position the position in the XY plane when the biological sample image SIM3 is acquired by moving the movable stage 11 only in the Z axis direction. The biological sample image acquiring unit 42 exposes the imaging device 30 to acquire a biological sample image shown in FIG. 26B while the movable stage 11 is being moved.

In the biological sample images SIM3 and SIM4, the bright points BP10 and BP12 are images of the same fluorescent marker EM and the bright points BP11 and BP13 are images of the same fluorescent marker EM.

At the time of acquiring the biological sample image SIM4, the movable stage 11 is circularly moved in the XY plane about the position in the XY plane when the biological sample image SIM 3 is acquired. Accordingly, the center of the bright point BP12 (the center of the circular-arc) in the biological sample image SIM3 is the same as the center of the bright point BP10.

Therefore, the CPU 21 calculates the center positions (the coordinates in the biological sample image SIM3) of the circular bright points BP10 and BP11 in the biological sample image SIM3. Then, the CPU 21 sets the positions (the same coordinates) in the biological sample image SIM4 corresponding to the calculated center positions in the biological sample image SIM3 as the centers of the circular-arc bright points BP12 and BP13.

The CPU 21 calculates the positions (coordinates) having the highest brightness level in the bright points BP12 and BP13, calculates the angles formed by the straight lines, which connect the centers to the positions having the highest brightness level, and the X axis, and calculates the positions in the Z axis direction of the fluorescent markers EM on the basis of the calculated angles.

Accordingly, compared with the case where the biological sample image SIM3 imaged by moving the movable stage 11 only in the Z axis direction is not used, since the center position in the circular-arc image is detected, it is possible to detect the position in the Z axis direction with higher precision.

In the fourth embodiment, the distance ΔZ in the Z axis direction between the fluorescent markers EM1 and EM2 is calculated using the elliptical image EIM imaged by moving the movable stage 11 in the Z axis direction at a constant speed and half-rotating the transparent plate 114 at the same time. The invention is not limited to this configuration, but the distance ΔZ in the Z axis direction between the fluorescent markers EM1 and EM2 may be calculated using the elliptical image imaged by moving the movable stage 11 in the Z axis direction at a constant speed and fully rotating the transparent plate 114 at the same time.

Specifically, in the data acquiring process, the CPU 21 generates the sharpened image SIM2 to calculate the distance ΔXY in the XY plane, and images the elliptical image EIM to calculate the distance ΔZ in the Z axis direction, and calculates the actual distance Δ between the fluorescent markers EM1 and EM2.

Then, the CPU 21 acquires the elliptical image by moving the movable stage 11 in the Z axis direction at a constant speed and fully rotating the transparent plate 114 at the same time, for example, when the calculated actual distance Δ is smaller than a threshold value set to a value for measuring the actual distance Δ with higher precision.

Specifically, the CPU 21 controls the stage movement controller 41 to move the movable stage 11 in the Z axis direction at a constant speed so as to get close to the objective lens 12A, so that the focal plane FP of the objective lens 12A is moved from the cover glass CG side of the biological sample SPL to the slide glass SG side.

The imaging position movement controller 43 fully rotates the transparent plate 114 via the motor 111 while the focal plane FP is being moved from the cover glass CG side of the biological sample SPL to the slide glass SG side.

The biological sample image acquiring unit 42 exposes the imaging device 30 to light to acquire the fluorescent image while the movable stage 11 and the transparent plate 114 are being moved by the stage movement controller 41 and the imaging position movement controller 43, and generates the elliptical image by connecting the fluorescent images of the sample regions.

The distance calculator 45 calculates the distance ΔZ' in the Z axis direction from the elliptical image imaged by fully rotating the transparent plate 114, by performing the same operation as calculating the distance ΔZ in the Z axis direction in the elliptical image EIM. Then, the distance calculator 45 calculates the actual distance Δ' between the fluorescent markers EM1 and EM2 using the distance ΔXY in the XY plane and the calculated distance ΔZ' in the Z axis direction.

Accordingly, the biological sample image acquiring apparatus 100 can calculate the actual distance ΔZ' between the fluorescent markers EM1 and EM2 with higher precision.

In the elliptical image imaged by fully rotating the transparent plate 114, the fluorescent markers EM separated from each other by the thickness corresponding to half the thickness of the biological sample SPL in the Z axis direction appear as the bright points BP having the same angle θ.

Accordingly, the biological sample image acquiring unit 42 can acquire the fluorescent image by ending the exposure of the imaging device 30 when the transparent plate 114 is half-rotated in the course of fully rotating the transparent plate 114, and can acquire the fluorescent image by exposing the imaging device 30 while the transparent plate 114 is being rotated by the second half.

In this case, it is possible to prevent the fluorescent markers EM different in position in the Z axis direction in the two fluorescent images from appearing as the bright points BP having the same angle θ in the elliptical image.

In the fourth embodiment, the sharpened image PIM imaged by moving the movable stage 11 only in the Z axis direction is acquired and the distance ΔXY in the XY plane between the bright points BP1 and BP2 is calculated from the sharpened image PIM. The invention is not limited to this configuration, but the distance ΔXY in the XY plane and the spacing ΔZ in the Z axis direction may be calculated from only the elliptical image EIG without acquiring the sharpened image PIM.

In the first to fourth embodiments, the objective lens 12A is disposed as the objective lens, the imaging device 30 is disposed as the imaging device, the stage movement controller 41 is disposed as the movement controller, and the biological sample image acquiring unit 42 is disposed as the biological sample image acquiring unit. However, the invention may be provided with an objective lens, an imaging device, a movement controller, and a biological sample image acquiring unit having other configurations.

The invention can be applied to the fields of biological experiments, invention of medicines, patient follow-ups, and the like.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A biological sample image acquiring apparatus comprising:
    an objective lens magnifying a region of a biological sample;
    an imaging device imaging the region magnified by the objective lens;
    a movement controller moving the focus of the objective lens in the thickness direction of the target region of the biological sample and moving the image of the region, which is magnified by the objective lens to be imaged onto the imaging device, in an in-plane direction; and
    a biological sample image acquiring unit acquiring a biological sample image of the region by exposing the imaging device to light while the movement controller is moving the image of the region,
    wherein the movement controller moves at least one of the focus of the objective lens and the image of the region separate from any movement of the biological sample according to a programmed routine, and
    wherein the imaging device is configured to image the region of the biological sample while the movement controller concurrently moves i) the focus of the objective lens in the thickness direction from a cover glass side to a slide glass side of the biological sample regardless of any focusing of the biological sample and ii) the image of the region in the in-plane direction.

2. The biological sample image acquiring apparatus according to claim 1, wherein the movement controller moves the focus of the objective lens in the thickness direction of the target region of the biological sample and moves the relative position of the biological sample and the imaging device in the in-plane direction.

3. The biological sample image acquiring apparatus according to claim 2, further comprising an extractor extracting the image of the biological sample obtained by removing noise, which results from the existence of wobble based on the movement by the movement controller, from the image acquired by the biological sample image acquiring unit.

4. The biological sample image acquiring apparatus according to claim 2, wherein the movement controller moves the relative position of the biological sample and the imaging device in the in-plane direction so as to change the moving speed while moving the focus of the objective lens in the thickness direction of the target region of the biological sample.

5. The biological sample image acquiring apparatus according to claim 2, wherein the movement controller moves the relative position of the biological sample and the imaging device in the in-plane direction so as to change the moving direction while moving the focus of the objective lens in the thickness direction of the target region of the biological sample.

6. The biological sample image acquiring apparatus according to claim 5, wherein the movement controller circularly moves the relative position of the biological sample and the imaging device in the in-plane direction while moving the focus of the objective lens in the thickness direction of the target region of the biological sample.

7. The biological sample image acquiring apparatus according to claim 1, further comprising an imaging position moving unit disposed between the objective lens and the imaging device so as to circularly move the image of the region imaged by the imaging device without changing its direction under the control of the movement controller.

8. The biological sample image acquiring apparatus according to claim 7, wherein the imaging position moving unit includes a shaft disposed to be parallel to an optical axis between the objective lens and the imaging device, a driver rotating the shaft, and a parallel plate fixed to be inclined at a predetermined angle in relation to the shaft, partially disposed between the objective lens and the imaging device, and transmitting the image of the region magnified by the objective lens.

9. The biological sample image acquiring apparatus according to claim 7, further comprising an emission filter disposed between the objective lens and the imaging device so as to transmit the image of the region magnified by the objective lens and block light other than the image of the region,
wherein the imaging position moving unit circularly moves the image of the region magnified by the objective lens without changing the direction thereof by moving the emission filter.

10. The biological sample image acquiring apparatus according to claim 6, further comprising:
a light source applying light for exciting a fluorescent marker as a target label to the biological sample which is stained with the fluorescent marker; and
a processor extracting a fluorescent image emitted from the fluorescent marker as the target label in the biological sample as a bright point, calculating the slope of the extracted bright point, and calculating the position of the fluorescent marker corresponding to the bright point in the thickness direction based on the calculated slope of the bright point.

11. The biological sample image acquiring apparatus according to claim 10, wherein the movement controller moves the focus of the objective lens only in the thickness direction of the target region of the biological sample and circularly moves the relative position of the biological sample and the imaging device in the in-plane direction about the position of the focus of the objective lens moved only in the thickness direction while moving the focus of the objective lens in the thickness direction of the target region of the biological sample, and
wherein the processor calculates the slope of the bright point on the basis of the biological sample image acquired when the movement controller moves the focus of the objective lens only in the thickness direction and the biological sample image acquired when the movement controller circularly moves the relative position while moving the focus of the objective lens in the thickness direction.

12. A biological sample image acquiring method comprising:
moving the focus of an objective lens in the thickness direction of a target region of a biological sample magnified by the objective lens and moving the image of the region, which is magnified by the objective lens to be imaged onto an imaging device, in an in-plane direction; and
acquiring a biological sample image of the region by exposing the imaging device to light during the movement,
wherein at least one of the focus of the objective lens and the image of the region is moved separate from any movement of the biological sample according to a programmed routine while the biological sample image is acquired, and
wherein the imaging device is configured to image the region of the biological sample while i) the focus of the objective lens is moved in the thickness direction from a cover glass side to a slide glass side of the biological sample regardless of any focusing of the biological sample and ii) the image of the region is moved in the in-plane direction.

13. A machine-accessible device having executable instructions, which when executed by a computer, cause the computer to perform the steps of:
moving the focus of an objective lens in the thickness direction of a target region of a biological sample magnified by the objective lens and moving the image of the region, which is magnified by the objective lens to be imaged onto an imaging device, in an in-plane direction; and
acquiring a biological sample image of the region by exposing the imaging device to light during the movement,
wherein at least one of the focus of the objective lens and the image of the region is moved separate from any movement of the biological sample according to a programmed routine while the biological sample image is acquired, and
wherein the imaging device is configured to image the region of the biological sample while i) the focus of the objective lens is moved in the thickness direction from a cover glass side to a slide glass side of the biological sample regardless of whether the biological sample comes into focus and ii) the image of the region is moved in the in-plane direction.

14. The biological sample image acquiring apparatus according to claim 1, wherein the movement controller moves at least one of the focus of the objective lens and the image of the region such that a fluorescent marker associated with the biological sample is (i) blurred in a first image of the biological sample, (ii) in focus in a second image of the biological sample, and (iii) blurred in a third image of the biological sample, the first image being acquired before the second image and the third image and the second image being acquired before the third image.

15. The biological sample image acquiring apparatus according to claim 1, further comprising:
- a light source applying light for exciting a fluorescent marker as a target label to the biological sample which is stained with the fluorescent marker; and
- a processor configured to:
  - identify as a bright point a group of pixels in the biological sample image that have a brightness value greater than a first predetermined threshold value;
  - calculate a major/minor axis ratio of an outline of the bright point based on a major length and a minor length of the bright point; and
  - determine the bright point is a fluorescent marker if the major/minor axis ratio is greater than a second predetermined threshold value.

16. The biological sample image acquiring apparatus according to claim 1, wherein the movement controller moves at least one of the focus of the objective lens and the image of the region according to the programmed routine independent of instruction by a user.

17. The biological sample image acquiring apparatus according to claim 1, wherein the movement controller moves at least one of the focus of the objective lens and the image of the region separate from any movement of the biological sample according to the programmed routine so that noise can be distinguished from the biological sample.

* * * * *